United States Patent [19]

Shturman

[11] Patent Number: 5,314,438
[45] Date of Patent: May 24, 1994

[54] ABRASIVE DRIVE SHAFT DEVICE FOR ROTATIONAL ATHERECTOMY

[75] Inventor: Leonid Shturman, Minneapolis, Minn.

[73] Assignee: Shturman Cardiology Systems, Inc., Minnetonka, Minn.

[21] Appl. No.: 12,444

[22] Filed: Feb. 2, 1993

Related U.S. Application Data

[63] Continuation-in-part of Ser. No. 992,415, Dec. 17, 1992.

[51] Int. Cl.$^5$ .............................................. A61B 17/32
[52] U.S. Cl. ................................... 606/159; 606/170; 606/180
[58] Field of Search .............. 606/159, 170, 171, 180; 604/22, 96

[56] References Cited

U.S. PATENT DOCUMENTS

| | | |
|---|---|---|
| Re. 33,569 | 4/1991 | Gifford, III et al. . |
| Re. 33,911 | 5/1992 | Samson et al. . |
| 4,445,509 | 5/1984 | Auth . |
| 4,679,557 | 7/1987 | Opie et al. . |
| 4,781,186 | 11/1988 | Simpson et al. . |
| 4,926,858 | 5/1990 | Gifford, III et al. . |
| 4,979,951 | 12/1990 | Simpson . |
| 4,990,134 | 2/1991 | Auth . |
| 5,047,040 | 9/1991 | Simpson et al. . |
| 5,053,044 | 10/1991 | Mueller et al. . |
| 5,067,489 | 11/1991 | Lind . |
| 5,071,424 | 12/1991 | Reger . |
| 5,074,871 | 12/1991 | Groshong . |
| 5,217,474 | 6/1993 | Zacca et al. ......................... 606/170 |

FOREIGN PATENT DOCUMENTS

| | | |
|---|---|---|
| 0359447 | 3/1990 | European Pat. Off. . |
| 9004657 | 8/1990 | PCT Int'l Appl. . |
| 9101813 | 3/1991 | PCT Int'l Appl. . |
| 9105844 | 8/1991 | PCT Int'l Appl. . |

OTHER PUBLICATIONS

"Premier Two Striper® Crown & Bridge Techniques," Abrasive Technology, Inc., Westerville, Ohio, USA.

Tupac, Robert G., et al, "A Comparison of Cord Gingival Displacement with the Gingitage Technique," *The Journal of Prosthetic Dentistry*, Nov. 1981, vol. 46, No. 5, pp. 509-515.

(List continued on next page.)

*Primary Examiner*—Stephen C. Pellegrino
*Assistant Examiner*—William Lewis
*Attorney, Agent, or Firm*—Gregory P. Kaihoi

[57] ABSTRACT

An abrasive drive shaft atherectomy device for removing stenotic tissue from an artery. The device includes a flexible, elongated drive shaft having a central lumen for receipt of a guide wire therein and around which the drive shaft may be rotated. The drive shaft is made from one or more helically wound wires. Wire turns of the proximal segment of the drive shaft have a generally constant diameter. Wire turns of a segment of the drive shaft near its distal end have an enlarged diameter. At least part of the enlarged diameter segment includes an external coating of an abrasive material to define an abrasive segment of the drive shaft which, when rotated at high speeds, is usable to remove stenotic tissue from an artery. In a preferred embodiment, the device includes a bushing disposed in the enlarged diameter segment for supporting the enlarged diameter turns of the drive shaft. A gap may be provided in the turns of the drive shaft to permit imaging therethrough by an ultrasound imaging device disposed in the central lumen of the drive shaft. Preferably the drive shaft is made from inner and outer coaxial wire layers helically wound in opposite directions so that the outer layer tends to radially contract and the inner layer tends to radially expand when the drive shaft is rotated in a predetermined direction. In one such embodiment, a toroidal collar is positioned between the inner and outer layers of the enlarged diameter abrasive segment of the drive shaft.

114 Claims, 19 Drawing Sheets

OTHER PUBLICATIONS

*Atherectomy, A Physician's Guide*, Strategic Business Development, Inc., Kauai, Hawaii 96714 USA, 1990, pp. 1–114.

Bom, N., et al, "Early and Recent Intraluminal Ultrasound Devices," *International Journal of Cardiac Imaging*, 4:79–88, 1989.

"Rotablator®, a Revolution in Angioplasty," Heart Technology Inc., Bellevue, Washington 98005 USA.

McCarty, Lyle H., "Catheter Clears Coronary Arteries," *Design News*, Sep. 23, 1991, pp. 88–92.

"Premier Presents Two Striper® Dental Diamond Instruments," Abrasive Technology Inc., Westerville, Ohio USA.

Gilmore, H. W., et al, "Instrumentation," *Operative Dentistry*, 4th Ed., Ch. 4, pp. 55, 64–73, The C. V. Mosby Company, 1982.

Gilmore, H. W., et al, *Operative Dentistry*, 4th Ed., pp. 348–351, 353–354, The C. V. Mosby Company, 1982.

"Premier Two Striper® Gingival Curettage," Abrasive Technology Inc., Westerville, Ohio USA.

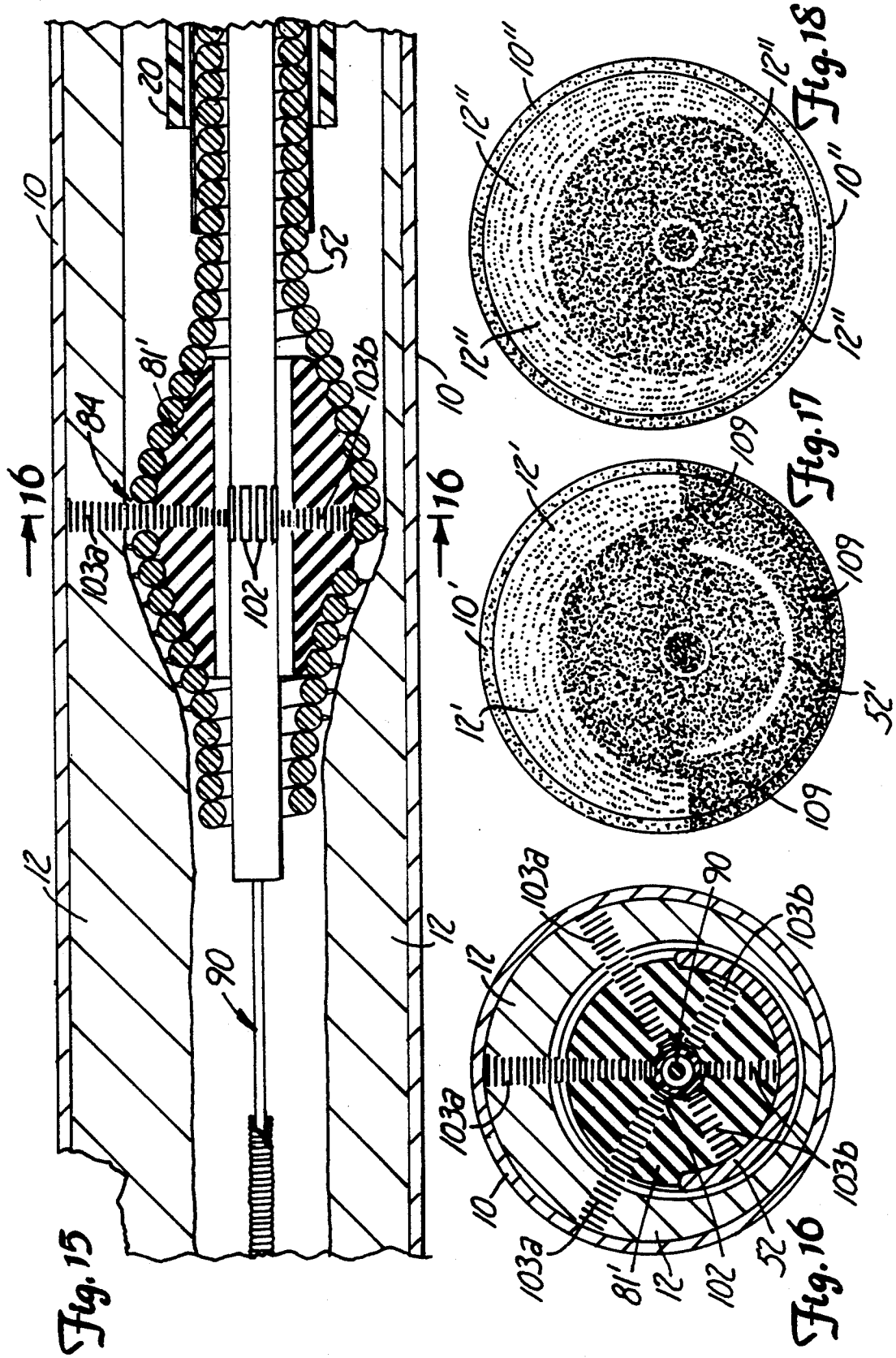

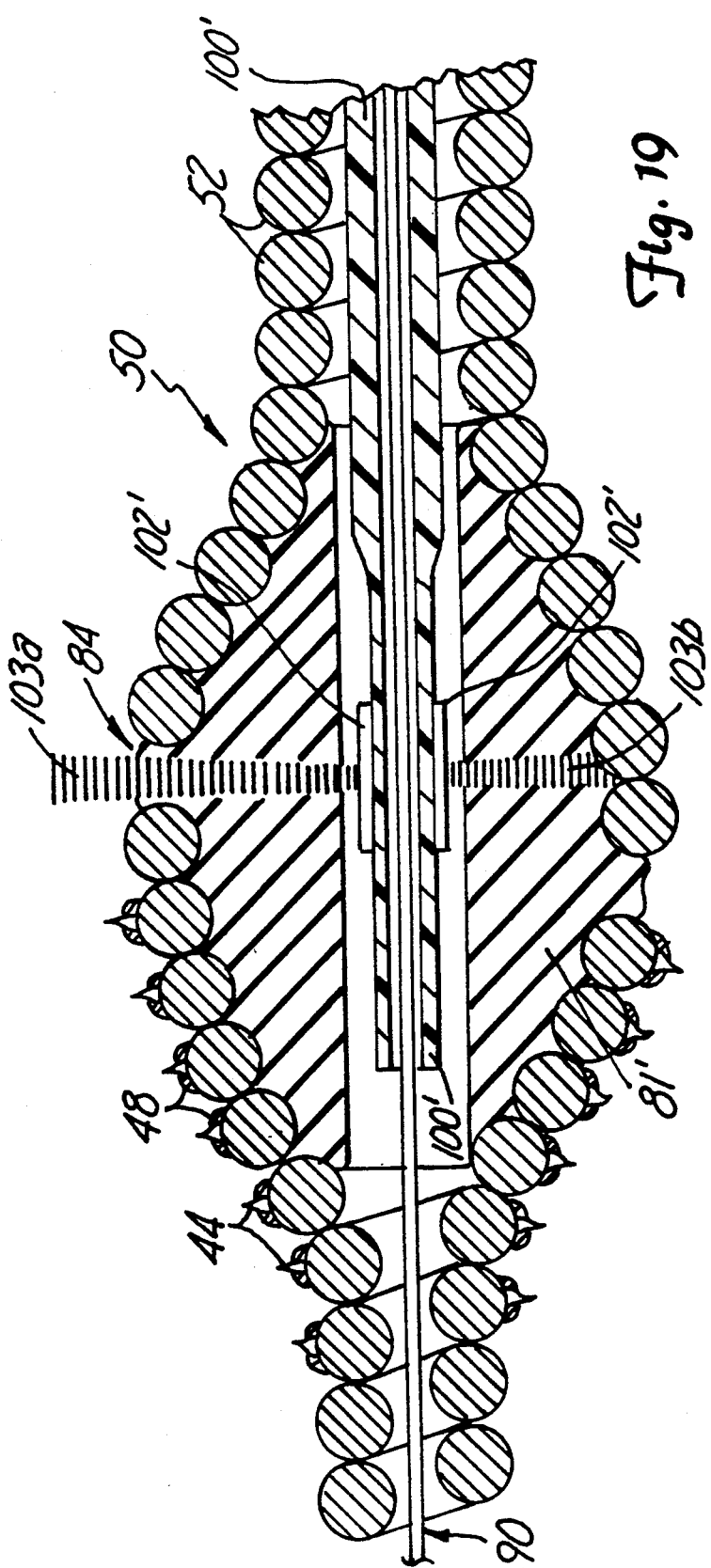

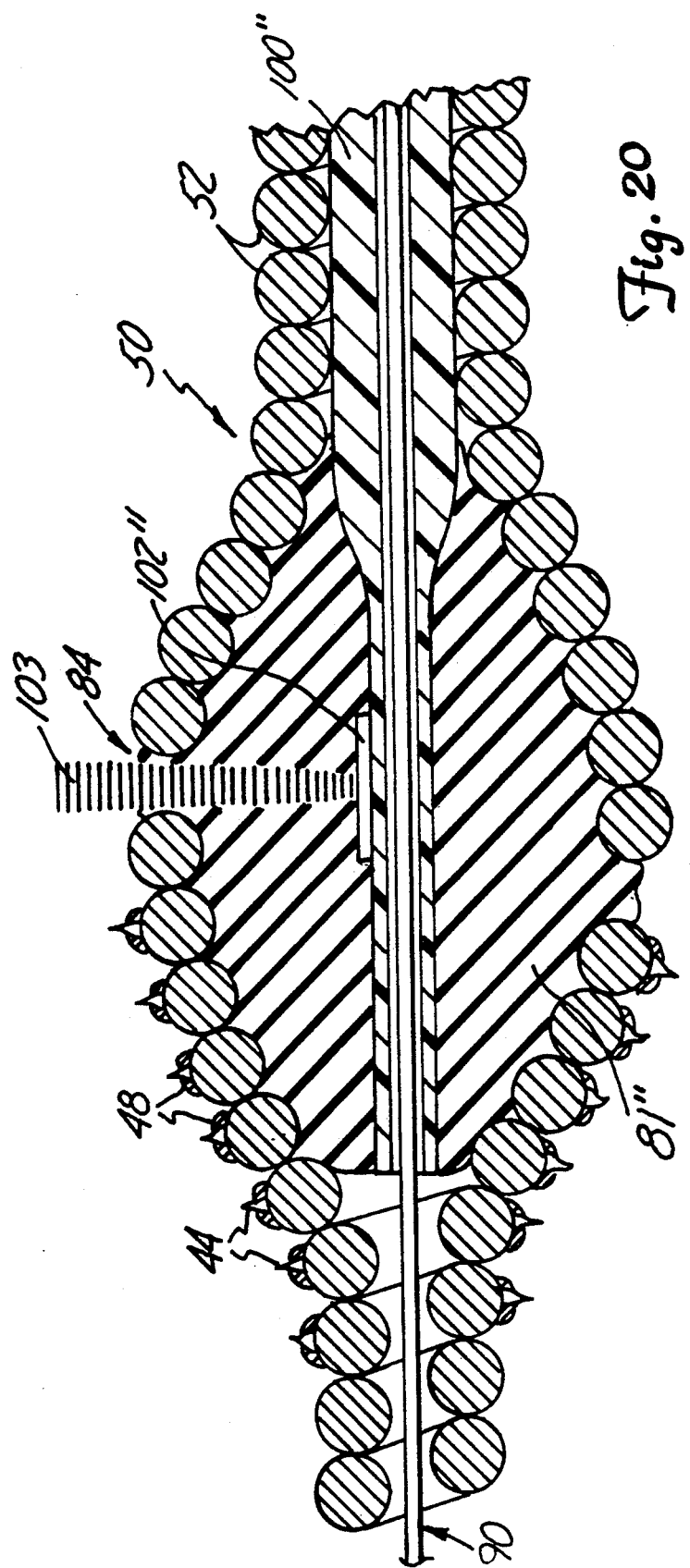

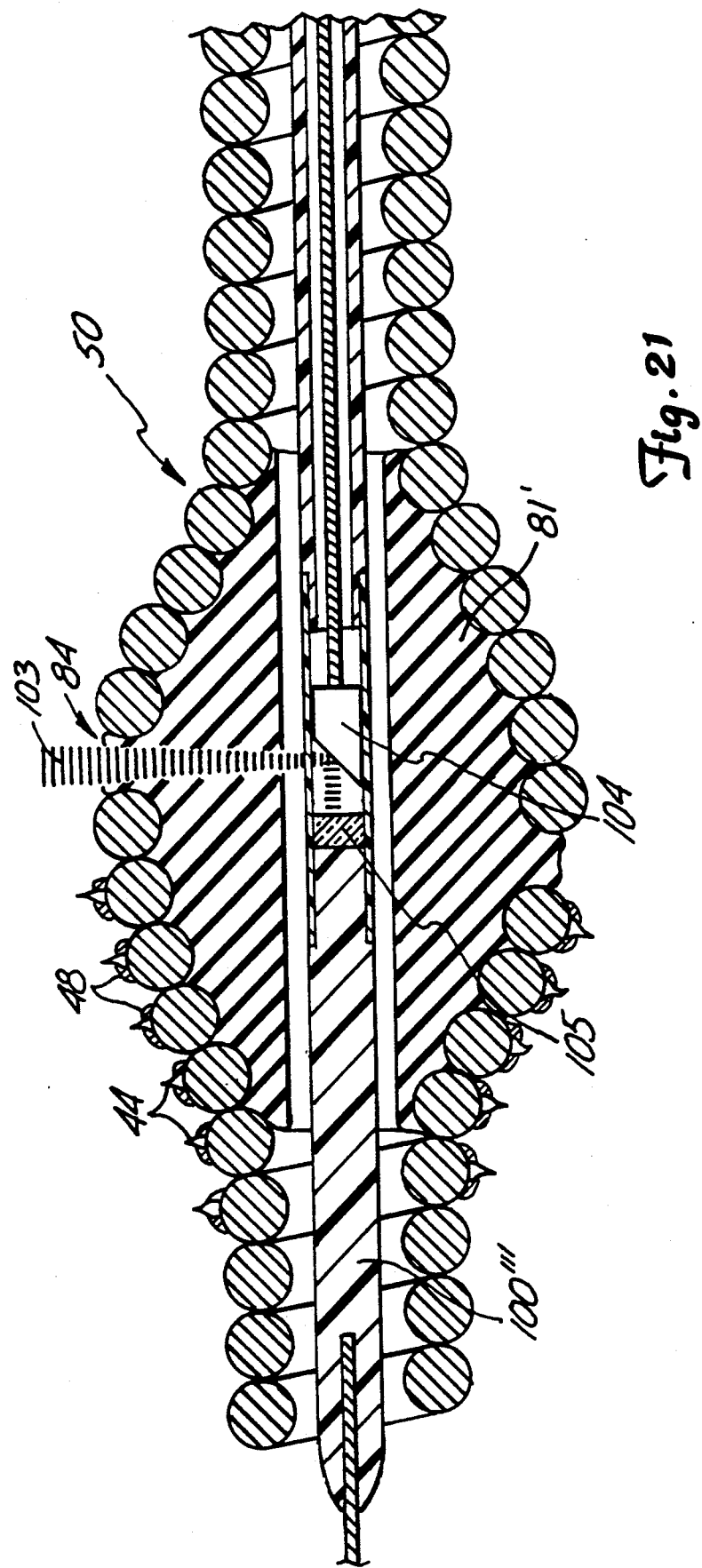

ABRASIVE DRIVE SHAFT DEVICE FOR ROTATIONAL ATHERECTOMY

RELATED APPLICATION

This application is a continuation in part of U.S. application Ser. No. 07/992,415, filed Dec. 17, 1992, now pending.

FIELD OF THE INVENTION

The invention relates to devices and methods for removing tissue from body passageways, such as removal of atherosclerotic plaque from arteries, utilizing a rotary atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (issued to Auth), a rotating buff covered with an abrasive cutting material such as diamond grit (diamond particles or dust) is carried at the distal end of a flexible drive shaft. The ability of diamond dust covered buffs to remove human soft tissue at high surface speeds (e.g., small diameter buffs rotated at about 200,000 rpm) has been known for some time and has been utilized in dentistry since at least the early 1980's to remove soft gum tissue (see, e.g., "Premier Two Striper® Gingival Curettage" (Abrasive Technology, Inc. 1982); "Premier Two Striper's Crown & Bridge Techniques" (Abrasive Technology, Inc. 1981); H. Gilmore, et. al, *Operative Dentistry* (C. V. Mosby Company 1982, 4th ed.), pp. 64–65, 69, 348–350; R. Tupac, et al., "A Comparison of Cord Gingival Displacement With the Gingitage Technique," *Journal of Prosthetic* (Nov. 1981, pp.509–515); and Premier Presents Two Striper® Dental Diamond Instruments (Abrasive Technology, Inc. 1989). The buff in the Auth device and in such dental devices is rotated at speeds in the range of 20,000 to 200,000 rpm or more, which, depending on the diameter of the buff, can provide surface speeds of the abrasive particles on the buff in the range of 40 ft/sec. Auth claims that at surface speeds below 40 ft/sec the abrasive buff will remove hardened atherosclerotic material but will not damage normal elastic soft tissue of the vessel wall. Auth also admits that at surface speeds above 40 ft/sec the abrasive burr will remove both hardened and soft tissue. See, e.g., U.S. Pat. No. 4,990,134 at col. 3, lines 20–23.

Unfortunately, not all atherosclerotic plaques are hardened, calcified atherosclerotic plaques. Moreover, the mechanical properties of the soft plaques are very often quite close to the mechanical properties of the soft wall of the vessel. Thus, one cannot safely rely entirely on the differential cutting properties of such abrasive burrs to remove atherosclerotic material from an arterial wall, particularly where one is attempting to remove all or almost all of the atherosclerotic material. See, e.g., *Atherectomy, A Physicians Guide*, (Strategic Business Development, Inc., 1990), pp. 89, 94–96. Furthermore, in clinical practice, the Auth buff is virtually always rotated at speeds of at least about 155,000 rpm. At such speeds a diamond dust covered buff with a diameter of 1.5 mm achieves a surface speed of 40 ft/sec, the very speed at which the differential cutting effect becomes limited, at best (i.e., the buff removes both hard and soft tissue).

Thus, a significant drawback has been recognized in use of the Auth-type of buff. Although under some conditions the differential cutting properties of such buffs are effective to protect healthy tissue, in many circumstances the buff nevertheless can abrade at least a portion of the healthy tissue, creating a risk of perforation. This is particularly true at higher rotational speeds. A majority of atherosclerotic lesions are asymmetrical (i.e., the atherosclerotic plaque is thicker on one side of the artery than on the other). Moreover, pressure of the buff against the atherosclerotic plaque is achieved only by the use of a buff having a diameter slightly larger than the opening through the stenotic passageway. Thus, since the stenotic material will be entirely removed on the thinner side of an eccentric lesion before it will be removed on the other, thicker side of the lesion, during removal of the remaining thicker portion of the atherosclerotic plaque the buff necessarily will be engaging healthy tissue on the side which has been cleared—-indeed, lateral pressure by such healthy tissue against the buff is required to keep the buff in contact with the remaining stenotic tissue on the opposite wall of the passageway. Thus, in clinical practice (balancing safety and residual stenosis), physicians typically used an undersized buff and are not able to remove the entire stenosis—e.g., on a patient having a coronary artery with an original diameter estimated to be 3 mm, rarely would a physician use a buff diameter of more than about 2 mm. See, e.g., *Atherectomy, A Physicians Guide*, (Strategic Business Development, Inc., 1990), p. 96. These risks are enhanced at high rotational speeds where the differential cutting phenomenon is significantly diminished.

Typically, fluoroscopy is utilized to assist the physician in placing the Auth-type buff in the general location of a stenosis in an artery. This imaging technique does not provide cross-sectional imaging of the artery and, thus, significantly limits the ability of the physician to monitor in real-time the actual removal of stenotic tissue. As a result, the physician's ability to thoroughly remove the stenotic lesion is limited. Unfortunately, conventional intravascular ultrasound imaging equipment, which allows cross-sectional imaging of the arteries, cannot be used simultaneously with the Auth-type device for two reasons. First, the Auth buff itself completely occludes the stenotic portion of the artery during the procedure and therefore leaves no room for an intravascular ultrasound catheter to be positioned in the arterial passageway next to the buff. Second, the Auth-type buff is not sonolucent and therefore will not permit ultrasonic imaging from inside of the buff.

In addition, the Auth device has three drawbacks due to the fact that a separately manufactured abrasive buff must be attached to (or near) the distal end of the flexible drive shaft:

(1) First, the connection between the buff and the drive shaft is critical, in that it must be secure against failure. This requirement therefore adds to the cost of producing the device.

(2) Second, the size of the burr, particularly the diameter of the buff, necessarily limits the ability of the device to safely initiate opening of very tight stenotic lesions, particularly those located more distally in branches of major coronary arteries.

(3) Third, since the buff is made from a solid, inflexible metal, when it is used in tortuous arteries the length of the buff must be kept relatively short in order to allow the buff to navigate the bends and curves of the artery. For a buff of a given diameter, the length of the buff defines how rapidly the transition from its smallest diameter (close to the diameter of the drive shaft) to its maximum diameter must occur. A longer burr may have a more gently sloping profile, while a shorter buff must have a steeper profile. Thus, the inflexibility of the Auth-type buff requires the buff to be relatively blunt.

SUMMARY OF THE INVENTION

The invention provides a rotational atherectomy device that eliminates the three above-described drawbacks associated with the separate manufacturing and attachment of a burr for the Auth-type device. It also permits use of intravascular ultrasound imaging to monitor the removal of stenotic tissue as it is being removed, thus reducing the risk of perforation, particularly at high rotational speeds where the differential cutting phenomenon is significantly reduced, and allowing the physician to more completely remove stenotic tissue without substantially increasing the risk of perforation.

In one embodiment, the device comprises a rotational atherectomy device having a flexible, preferably multi-stranded, elongated drive shaft. The drive shaft includes a proximal segment having a generally constant cross-sectional diameter, a distal segment also having a generally constant cross-sectional diameter, and an intermediate segment having an enlarged cross-sectional diameter. This intermediate segment is comprised of two portions, a proximal portion and a distal portion. Wire turns of the proximal portion of the drive shaft's intermediate segment have diameters that progressively increase in diameter distally, and wire turns of the distal portion have diameters that progressively decrease in diameter distally. Thus, together the proximal and distal portions front an enlarged diameter intermediate segment of the drive shaft. A thin layer of abrasive particles is bonded to the wire turns of a portion (preferably the distal portion) of the intermediate segment of the drive shaft, thereby defining an abrasive segment of the drive shaft.

In a second embodiment, the wire turns of the enlarged-diameter intermediate segment include a gap (preferably formed by a temporary change in the pitch of the wire turns) which provides a window in the intermediate segment that is relatively transparent to ultrasonic energy (i.e., a "sonolucent window"). An intravascular ultrasound imaging catheter or an ultrasound imaging guide wire can be inserted through the lumen of the drive shaft to a position (or incorporated into the drive shaft at a position) where the ultrasonic transducer elements are aligned with the sonolucent window in the intermediate segment of the drive shaft, permitting ultrasonic imaging of a cross-section of the stenotic area (including the thickness and composition of the atherosclerotic plaque), and the relative position of the abrasive buff with respect to the stenotic tissue. As a result, intravascular ultrasound imaging permits real-time monitoring of the removal of the stenotic tissue, allowing the physician to more thoroughly remove the atherosclerotic tissue without substantially increasing the risk of vascular perforation.

In either embodiment, the drive shaft is generally comprised of a flexible helically wound multistrand wire coil. The abrasive material may be secured to the turns of the wire of the drive shaft coil by any suitable bonding material. The bonding material may be applied so as to not bond adjacent turns of the wire of the drive shaft coil to one another, thereby preserving the flexibility of the drive shaft throughout the abrasive segment. Alternately, the bonding material may be applied to the turns of the wire of the drive shaft coil so as to not only bond the abrasive material to the drive shaft but also to bond adjacent turns of the wire of the drive shaft coil to one another, thereby forming a generally nonflexible abrasive segment in the drive shaft.

A significant advantage of the device of the invention is that the diameter of an abrasive segment of the drive shaft may exceed the diameter of the drive shaft coil itself by an amount as little as the thickness of a circumferential layer of diamond particles (typically about 10–30 $\mu$m thick) and the thickness of a layer of bonding material (which usually does not exceed about 5–10 $\mu$m). Thus, the overall maximum diameter of the abrasive segment, including the thickness of the abrasive coating, may be only as little as about 25–90 $\mu$m larger than the maximum diameter of the wire turns of the abrasive segment of the drive shaft itself.

The invention solves the above-identified drawbacks of the Auth device in that:

(1) the invention does not require a separately manufactured buff to be attached to the drive shaft;

(2) the overall diameter of the abrasive segment for a given drive shaft can be made significantly smaller than an abrasive buff for the same diameter drive shaft, thereby allowing treatment of extremely tight stenotic lesions, particularly those located more distally in major coronary arteries or branches of such arteries;

(3) the abrasive segment can be made flexible and can be made longer (than an Auth-type buff of the same diameter), thus allowing the abrasive segment to have a very gently sloping profile, permitting, as a result, treatment of even very tortuous arteries; and (4) the invention permits use of intravascular ultrasound imaging to monitor the removal of stenotic tissue as it is being removed, thus reducing the risk of perforation, particularly at high rotational speeds where the differential cutting phenomenon is significantly reduced.

BRIEF DESCRIPTION OF THE DRAWINGS

FIG. 15 depicts the distal portion of the abrasive drive shaft atherectomy device of FIG. 9 being advanced across a stenotic segment of an artery;

FIG. 16 is a cross-sectional view of FIG. 15, taken along line 16—16 thereof;

FIG. 17 represents the instantaneous cross-sectional ultrasound image corresponding to FIG. 16;

FIG. 18 represents the electronically reconstructed composite cross-sectional ultrasound image corresponding to FIG. 16;

FIG. 19 shows an embodiment similar to FIG. 14, but with a rotatable ultrasound catheter carrying two transducer elements oriented 180" from one another, and with the distal segment of the drive shaft having a smaller diameter than the proximal segment and being rotatable directly over the guide wire;

FIG. 20 shows an embodiment similar to FIG. 19, but with a single transducer element ultrasound catheter being secured to the abrasive drive shaft and being rotatable together with the drive shaft;

FIG. 21 shows another embodiment similar to FIG. 14, but with a rotating acoustic reflector type of ultrasound catheter.

BEST MODE FOR CARRYING OUT THE INVENTION

Although the drawings illustrate use of the abrasive drive shaft device of the invention in connection with removal of atherosclerotic plaques in arteries, the device is usable in other capacities, wherever tissue or obstructions are desired to be removed from body passageways, cavities, or any organ or organ system of the body.

Figure 1:
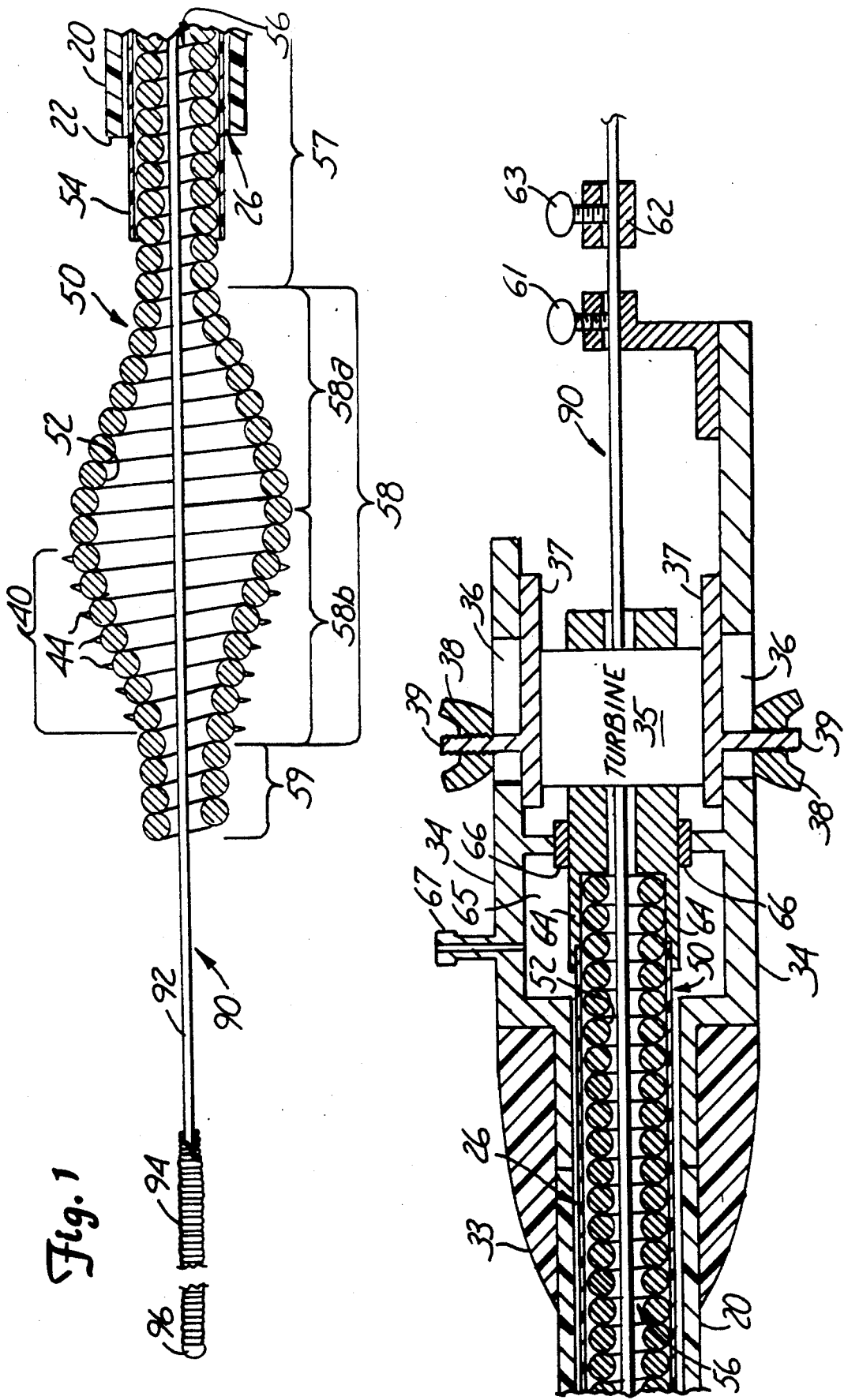
FIG. 1 is a partially broken away view of the proximal and distal end portions of one embodiment of the abrasive drive shaft atherectomy device of the invention, shown somewhat schematically and in longitudinal cross-section.

FIG. 1 illustrates the principal components of one embodiment of the device. An elongated catheter 20 with a distal end 22 includes a lumen 26. In this lumen 26 of the catheter 20, a helically wound flexible drive shaft 50 is disposed.

The drive shaft 50 preferably is multi-stranded. For the sake of clarity the drawings depict mono-filar or bi-filar drive shafts, in practice multi-filar drive shafts—particularly bi-filar or tri-filar drive shafts—may be preferred, but the principles illustrated in the drawings are equally applicable regardless of the number of wire strands making up the drive shaft. The drive shaft includes a proximal segment 57 having a generally constant cross-sectional diameter, a distal segment 59 also preferably having a generally constant cross-sectional diameter, and an intermediate segment 58 having an enlarged cross-sectional diameter. This intermediate segment may be considered to have two portions, a proximal portion 58a and a distal portion 58b. To achieve the enlarged diameter of the intermediate segment 58, wire turns of the proximal portion 58a of the drive shaft's intermediate segment have diameters that progressively increase in diameter distally, and wire turns of the distal portion 58b have diameters that progressively decrease in diameter distally. Thus, together the proximal and distal portions 58a and 58b define an enlarged diameter intermediate segment of the drive shaft.

A thin, flexible sheath 54 made from polytetrafluoroethylene (i.e., TEFLON®), or a similar low-friction material, may be provided, encasing at least two relatively short portions of the proximal segment of the drive shaft (one just proximal to the intermediate segment, and the other at the proximal end of the drive shaft). If desired, this sheath 54 may be extended to cover substantially the entire portion of the drive shaft 50 proximal to the intermediate segment 58. If desired, the distal segment 59 of the drive shaft 50 may also be coated with a TEFLON ® sheath (not shown in the drawings). In addition to, or in lieu of, the outer TEFLON ® sheath 54, the wire from which the helically wound drive shaft 50 is manufactured may be coated with a very thin layer (e.g., 0.0002–0.0004 inches) of TEFLON ® before it is helically wound, resulting in a drive shaft entirely coated with flexible TEFLON ®. Rotation of such a TEFLON ® coated drive shaft over a TEFLON ® coated guide wire 90 provides a very low friction TEFLON ®-TEFLON ® interface between the drive shaft and the guide wire and facilitates the use of higher rotational speeds.

A thin layer of abrasive particles 44 (shown somewhat schematically in the drawings) is bonded to the wire turns 52 of a portion (preferably at least the distal portion 58b) of the intermediate segment 58 of the drive shaft 50. The portion of the drive shaft covered with such abrasive particles 44 is referred to generally as the abrasive segment 40.

Preferably the abrasive particles are distributed over at least the distal portion 58a of the intermediate segment 58, and preferably this distal portion 58a of the intermediate segment 58 has a generally gently sloping profile so that the abrasive segment 40 engages the stenotic tissue somewhat gradually as the drive shaft is advanced in the artery. Other distributions of abrasive particles, and other shapes for the intermediate segment 58, can also be easily provided, as desired for a particular application. For example, coarser abrasive particles can be bonded on the more distal wire turns of the abrasive segment 40, and finer (polishing) abrasive particles can be bonded on the more proximal wire turns of the abrasive segment 40.

The lumen 56 of the flexible drive shaft 50 is sized to receive a conventional guide wire 90 having an elongated shaft 92 and a conventional helically wound distal tip portion 94, terminating in a rounded tip 96. The guide wire 90 can be provided with a slippery surface coating such as TEFLON ®, silicone, a combination of silicone over TEFLON ®, or similar slippery materials. A particularly slippery surface can be obtained by utilizing PHOTOLINK ® brand surface modification commercially available from Bio-Metric Systems, Inc. of Eden Prairie, Minn. The shaft of the guide wire 90 may be made of a shape-memory alloy, such as nitinol. The fabrication of the guide wire shaft from such a shape-memory alloy assures that the guide wire will not kink. The use of nitinol may also be advantageous compared to stainless steel in that nitinol will better dampen oscillations in the drive shaft.

The proximal segment 57 of the drive shaft 50 is disposed in a flexible catheter 20. The catheter 20 can be made from conventional catheter materials, including flexible thermoplastic or silicone materials. For example, the catheter preferably is made from a slippery material such as TEFLON ®. If necessary, the catheter 20 can be reinforced with an outer layer made of nylon or other similar materials having desirable torque transmitting characteristics. Thin wire braiding along substantially the entire length of the catheter may be also utilized if desired.

The proximal portion of the catheter 20, as shown in the lower half of FIG. 1, is secured to a housing 34. A turbine 35 (or equivalent source for rotational motion) is secured to a turbine mount 37 slidably received in the housing 34. Relative longitudinal sliding movement of the turbine mount 37 with respect to the housing 34 is permitted, and, when it is desired to lock the longitudinal position of the turbine 35 and turbine mount 37 with respect to the housing 34, wing nuts 38 can be tightened on threaded bolts 39 (which extend from the turbine mount 37 through slots 36 in the housing 34).

The turbine 35 is connected by way of turbine link 64 to the flexible drive shaft 50. A conventional seal 66 may be provided against the outer surface of the turbine link 64, preventing fluid from escaping from the cavity 65 while permitting rotational and longitudinal movement of the flexible drive shaft 50 and the turbine link 64. A side port 67 may be provided to permit infusion of lubricating fluid (such as saline or glucose solutions and the like) or radio-opaque contrast solutions into the cavity 65 and the lumen 26 of the catheter 20. The side port 67 could also be connected to a vacuum source for aspiration of fluid through the catheter lumen 26. Means may also be provided for infusing flushing fluid into the lumen 56 of the drive shaft 50 (around the guide wire 90). This may be accomplished, e.g., by coating the drive shaft with the TEFLON ® sheath 54 only over a relatively short length of the drive shaft proximal to its intermediate segment 58 and over a relatively short length at the proximal end of the drive shaft. Alternately, perforations or other suitable openings may be provided in the TEFLON ® sheath 54. In either case, such flushing fluid is allowed to flow between the wire turns 52 of the drive shaft 50 and into the lumen 56 of the drive shaft 50.

Set screw 61 is provided to selectively permit or prevent relative longitudinal movement of the guide wire 90 with respect to the housing 34. If the set screw 61 is loosened, the guide wire 90 can be advanced and retracted with respect to the housing 34 and the catheter 20. Alternately, tightening of set screw 61 against the guide wire 90 will prevent relative longitudinal movement of the guide wire 90 with respect to the housing 34 and catheter 20. With wing nuts 38 loosened, the turbine 35, turbine link 37 and drive shaft 50 (with its abrasive segment 40) can be moved longitudinally with respect to the guide wire 90, housing 34 and catheter 20. A guide wire handle 62 can be secured to the proximal end portion of the guide wire 90 by set screw 63 to facilitate manipulation of the guide wire 90.

Although the means for securing the guide wire 90, the turbine mount 37, and the housing 34 with respect to one another are illustrated in the drawing as being accomplished by use of wing nuts 38, and set screw 61, it will be appreciated that other conventional means or mechanisms (such as cam friction fittings, and the like) may easily be employed. Such cam friction fittings, etc., may also be used to attach the guide wire handle 62 to the guide wire 90. Moreover, the connection of the proximal end of the catheter 20 to the housing 34 (accomplished here by connector 33) and the side port 67 are shown somewhat schematically—any of a variety of conventional fittings that are readily commercially available or adaptable for this purpose may easily be employed.

Figure 2:
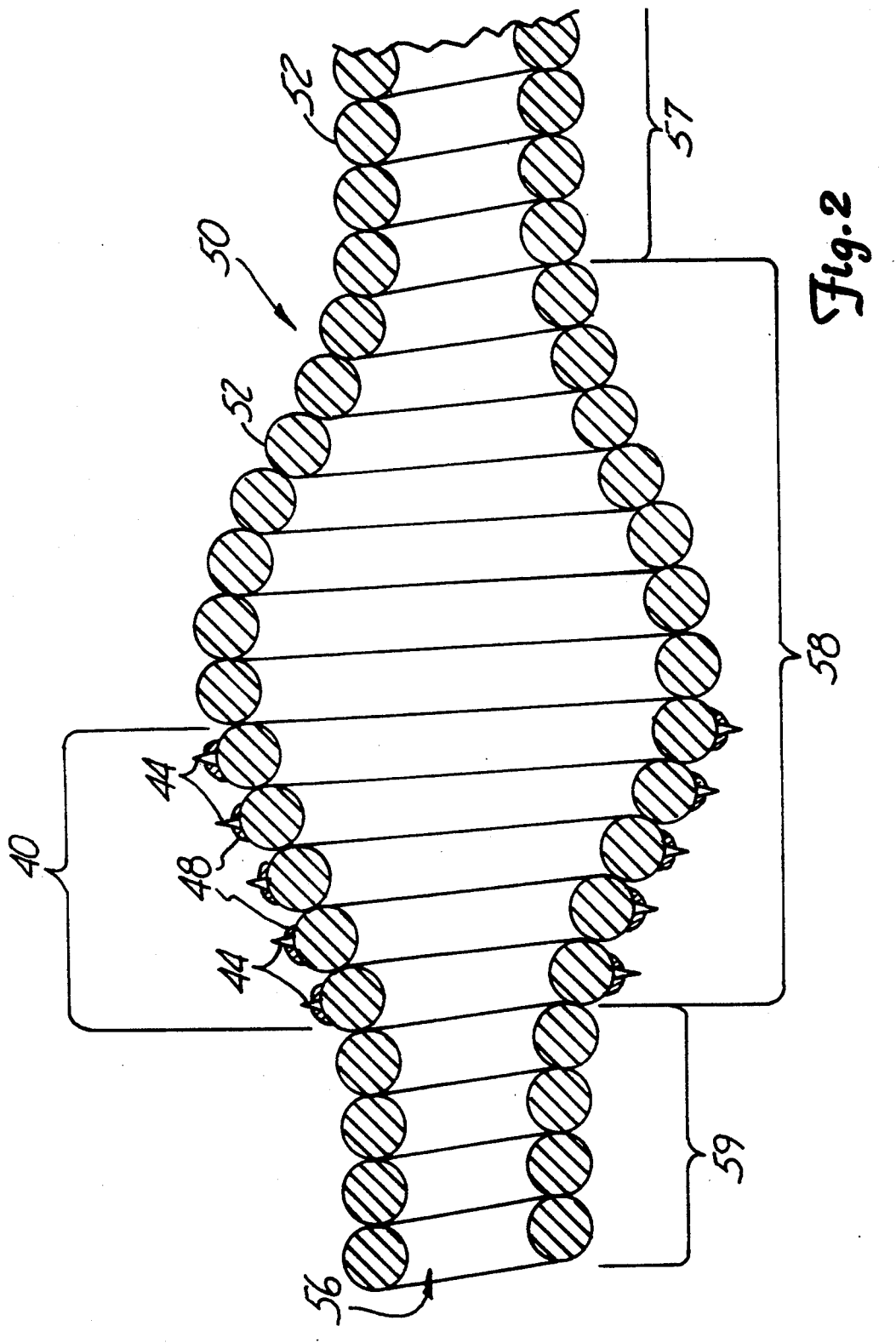
FIG. 2 is an enlarged, broken-away view in longitudinal cross-section of the abrasive drive shaft of the invention, with abrasive material shown somewhat schematically attached to the turns of the wire of the abrasive segment of the drive shaft, the abrasive material being attached in such a fashion that adjacent turns of the wire of the abrasive segment of the drive shaft are not secured to one another.

FIGS. 2–6 illustrate in enlarged, somewhat schematic fashion several alternate embodiments of the intermediate segment 58 of the drive shaft. Referring first to FIG. 2, abrasive particles 44 are secured to the turns or windings 52 of the drive shaft's abrasive segment 40 by a bonding material 48. The bonding material 48 has been applied to the turns of the wire of the drive shaft 50 in a fashion that effectively secures the abrasive particles 44 to the wire turns 52 of the drive shaft without securing the wire turns 52 of the drive shaft to one another. This provides the abrasive segment 40 of the drive shaft 50 with essentially the same degree of flexibility as the rest of the drive shaft.

The method for attaching the abrasive particles 44 to the surface of a the drive shaft may employ any of several well known techniques, such as conventional electroplating, fusion technologies (see, e.g., U.S. Pat. No. 4,018,576), brazing, adhesives and the like. The abrasive particles 44 themselves may be of any suitable composition, such as diamond powder, fused silica, titanium nitride, tungsten carbide, aluminum oxide, boron carbide, or other ceramic materials. Preferably they are comprised of diamond chips (or diamond dust particles). Abrasive materials of these types have been used in a variety of medical/dental applications for years and are commercially available. Attachment of abrasive particles to the wire turns of the drive shaft is also commercially available from companies such as Abrasive Technologies, Inc. of Westerville, Ohio.

Figure 3:
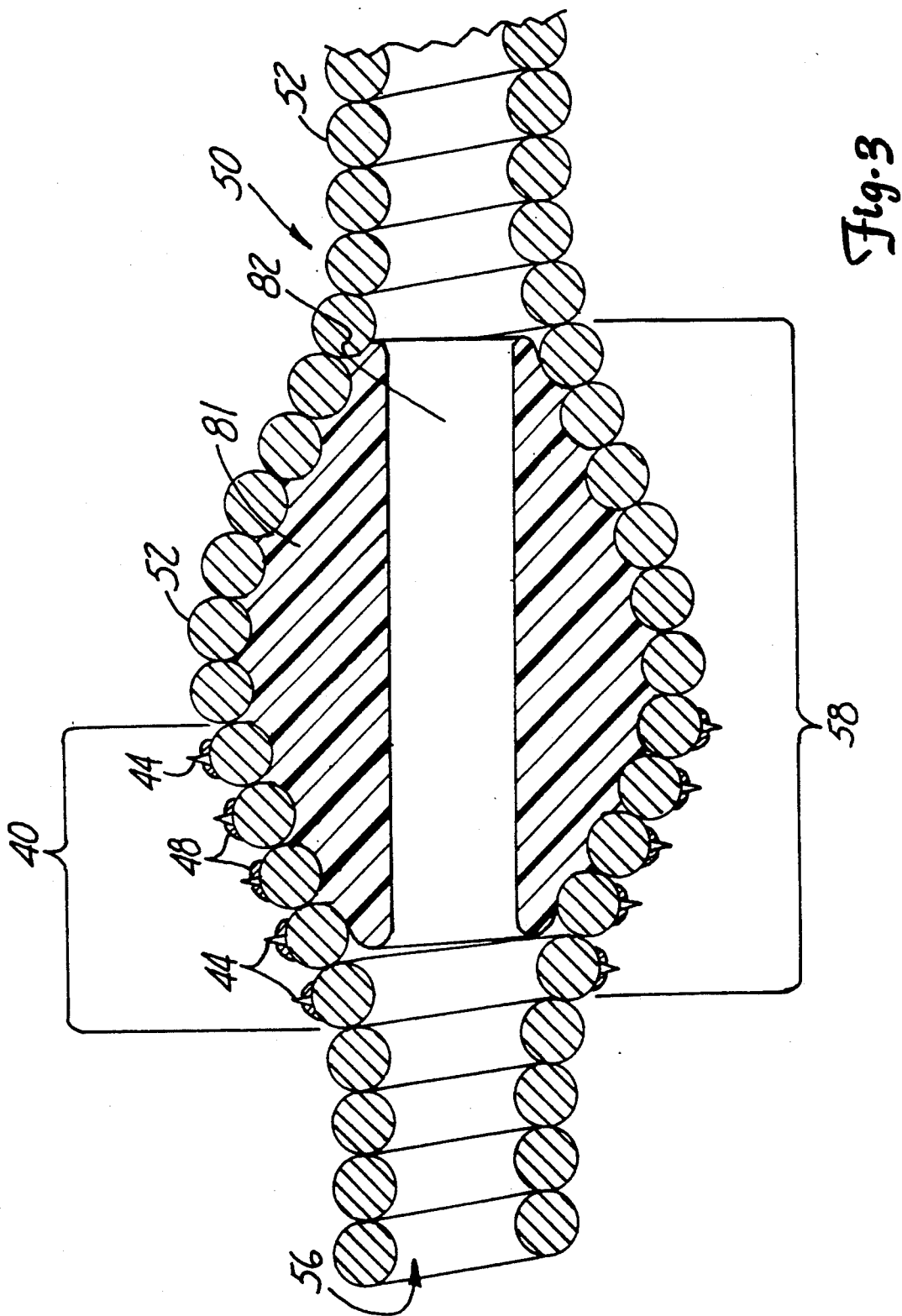
FIG. 3 is a view similar to FIG. 2, depicting a bushing supporting the enlarged diameter wire turns of the intermediate segment of the drive shaft.

FIG. 3 depicts a bushing 81 supporting the enlarged diameter wire turns of the intermediate segment 58 of the drive shaft. Such a bushing can be made of various suitable metals or plastics. Preferably it is made of a flexible material, thereby maintaining lateral flexibility in the intermediate segment 58. Also, desirably at least the surface of the bushing lumen 82 is made of (or coated with) a low friction material (e.g., TEFLON ®) to reduce friction between the bushing 81 and the guide wire 90, a particularly important feature when external radial forces on the intermediate segment are not symmetrical as the device is being used to remove stenotic tissue (particularly eccentric stenotic lesions in tortuous arteries).

Figure 4:
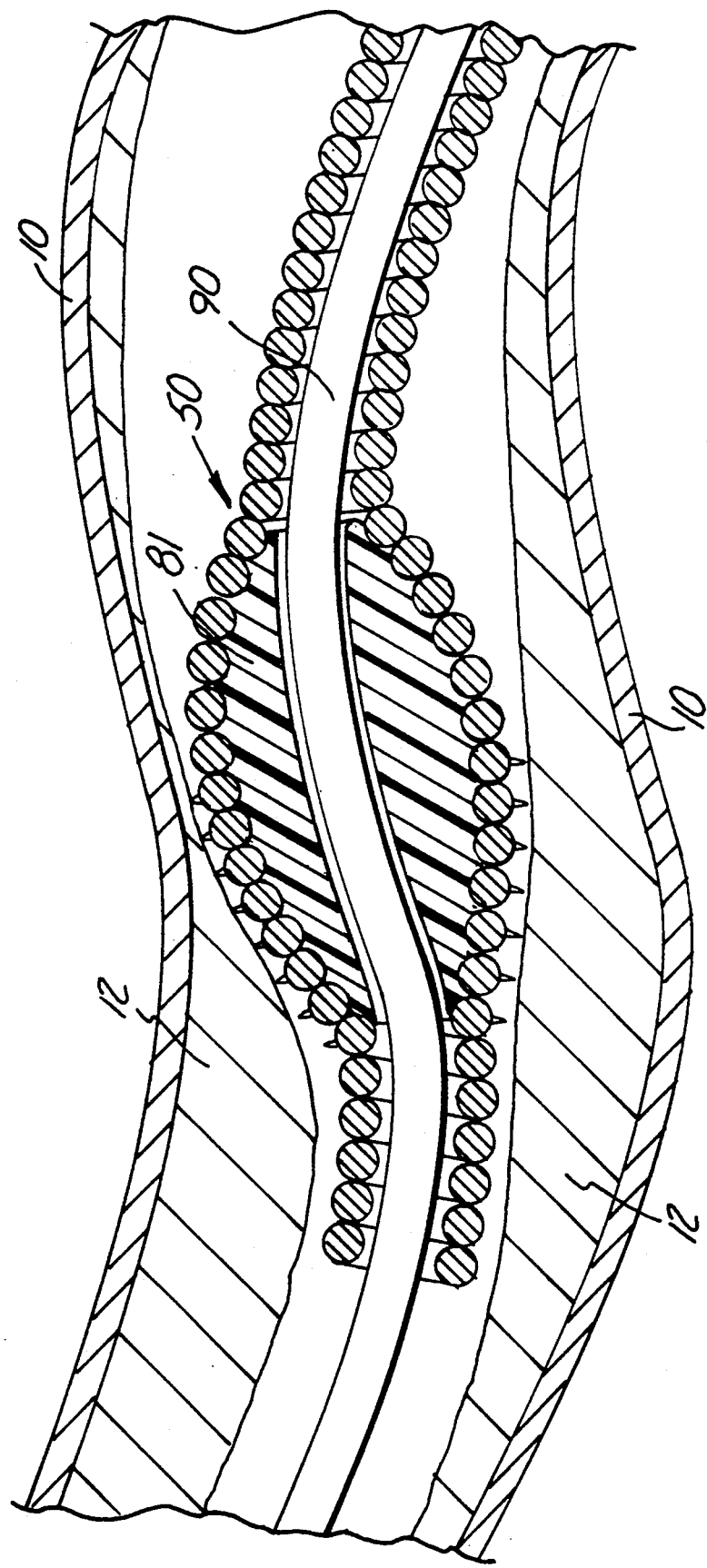
FIG. 4 depicts the flexible abrasive drive shaft atherectomy device of FIG. 3 inserted into a relatively tortuous artery, illustrating the flexibility of the intermediate segment of the drive shaft of the device, and the resulting benefit that the abrasive segment can be made somewhat elongated with a gently sloping profile.

FIG. 4 illustrates the advantage of the embodiment of FIG. 3 when used in tortuous arteries. In this drawing, the abrasive segment 40 of the drive shaft is being advanced, over the guide wire 90, across a stenosis 12 in a tortuous artery 10, removing stenotic tissue as it is advanced. The flexibility of the intermediate segment 58 (including the bushing 81) allows the device to follow the curves and bends of tortuous arteries. Moreover, since the intermediate segment 58 is flexible, the abrasive segment 40 can be made relatively longer than traditional Auth-type rigid buffs of the same diameter, thereby presenting a very gently sloping profile of the abrasive segment, without sacrificing the ability to travel through narrow, tortuous arteries. Such a profile allows the abrasive segment 40 to engage the stenotic tissue 12 somewhat more gradually than the more blunt Auth-type burr.

Figure 5:
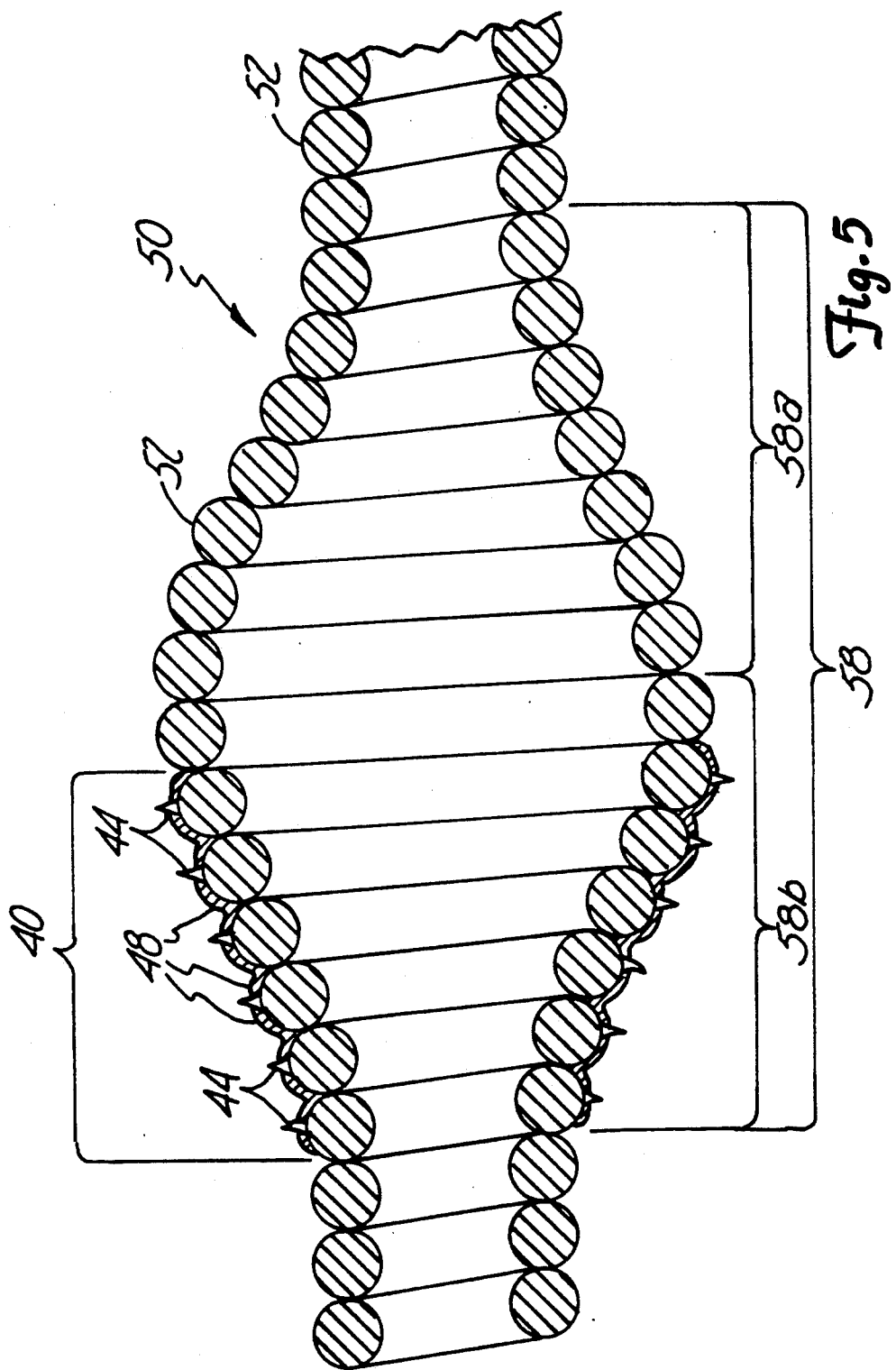
FIG. 5 shows another embodiment similar to FIG. 2 with bonding material not only attaching the abrasive material to the turns of the wire of the abrasive segment but also securing to one another the adjacent wire turns of the abrasive segment of the drive shaft.

FIG. 5 shows a somewhat different embodiment in that bonding material 48 is applied over the entire outer surface of the abrasive segment 40 of the drive shaft 50, thereby not only bonding the abrasive particles 44 to the wire turns 52 of the drive shaft 50, but also securing adjacent wire turns 52 of the drive shaft to one another, creating a relatively rigid abrasive segment 40 in the otherwise flexible drive shaft 50. In this embodiment the proximal portion 58a of the intermediate segment 58 remains flexible.

Figure 6:
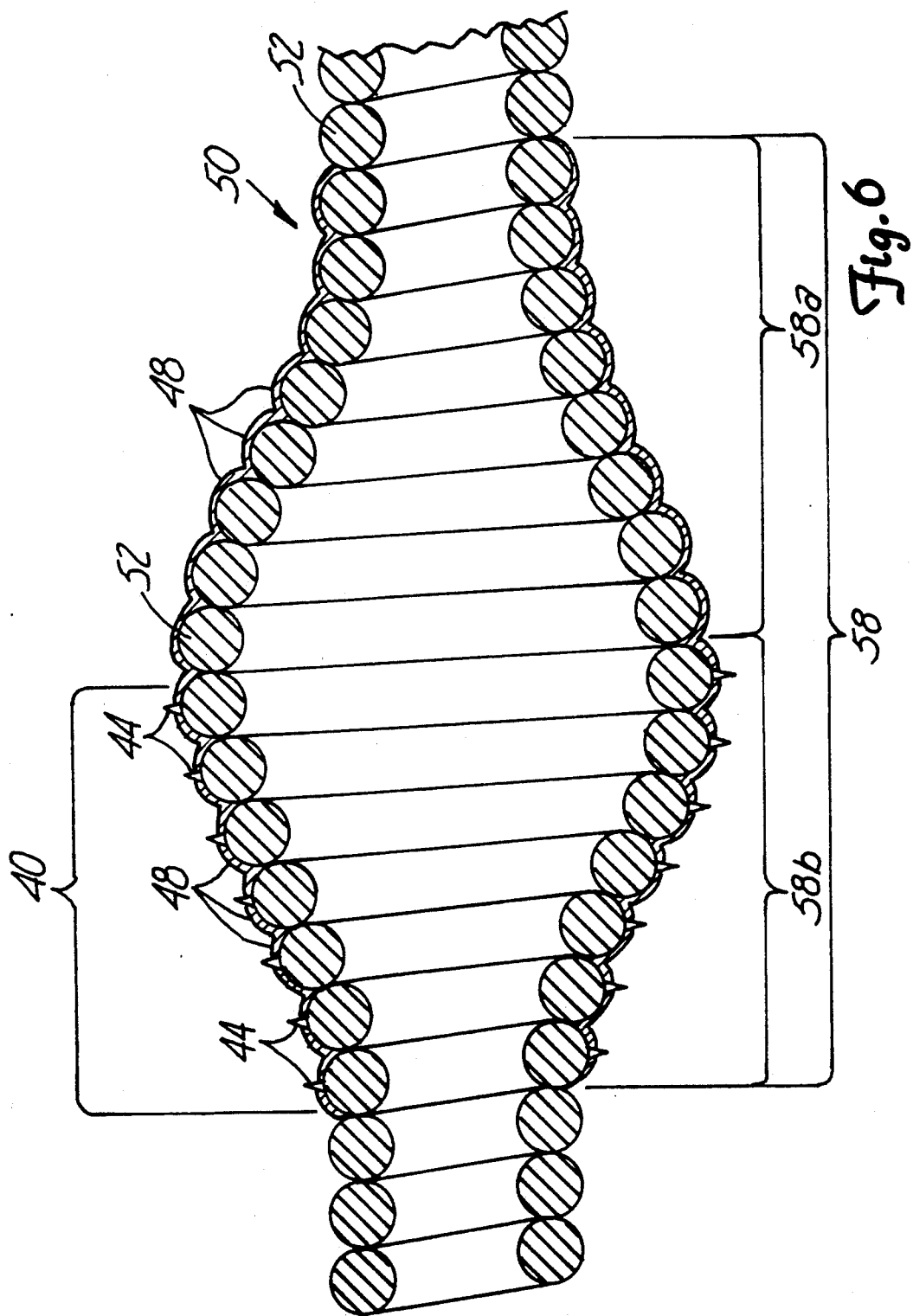
FIG. 6 is a modified embodiment similar to FIGS. 2 and 5 with the bonding material extending over and bonding together wire turns of the entire intermediate segment, thus making the entire intermediate segment substantially inflexible.

FIG. 6 is a modified embodiment similar to FIG. 5 with the bonding material 48 not only attaching the abrasive material 44 to the wire turns 52 of the abrasive segment 40 of the drive shaft 50 but also securing the wire turns 52 of the entire intermediate segment 58 of the drive shaft 50 to one another. Thus, although the abrasive segment 40 extends through only the distal portion 58a of the intermediate segment 58, the entire intermediate segment 58 is rendered substantially inflexible by the bonding material 48.

Figure 7:
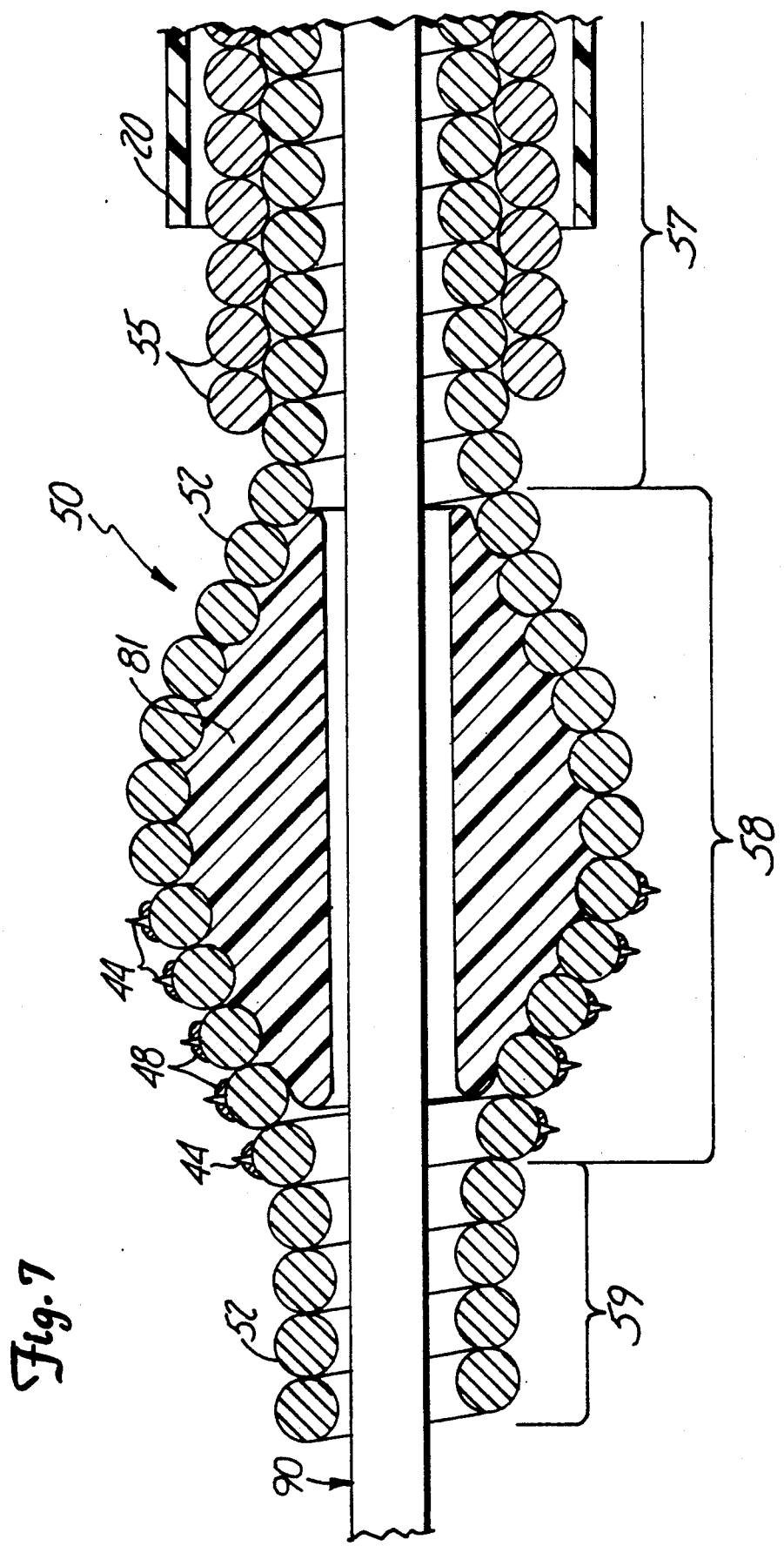
FIG. 7 depicts a modified embodiment similar to FIG. 3 but with the drive shaft having two helically wound layers, the outer layer terminating just proximal to the intermediate segment of the drive shaft.
Figure 8:
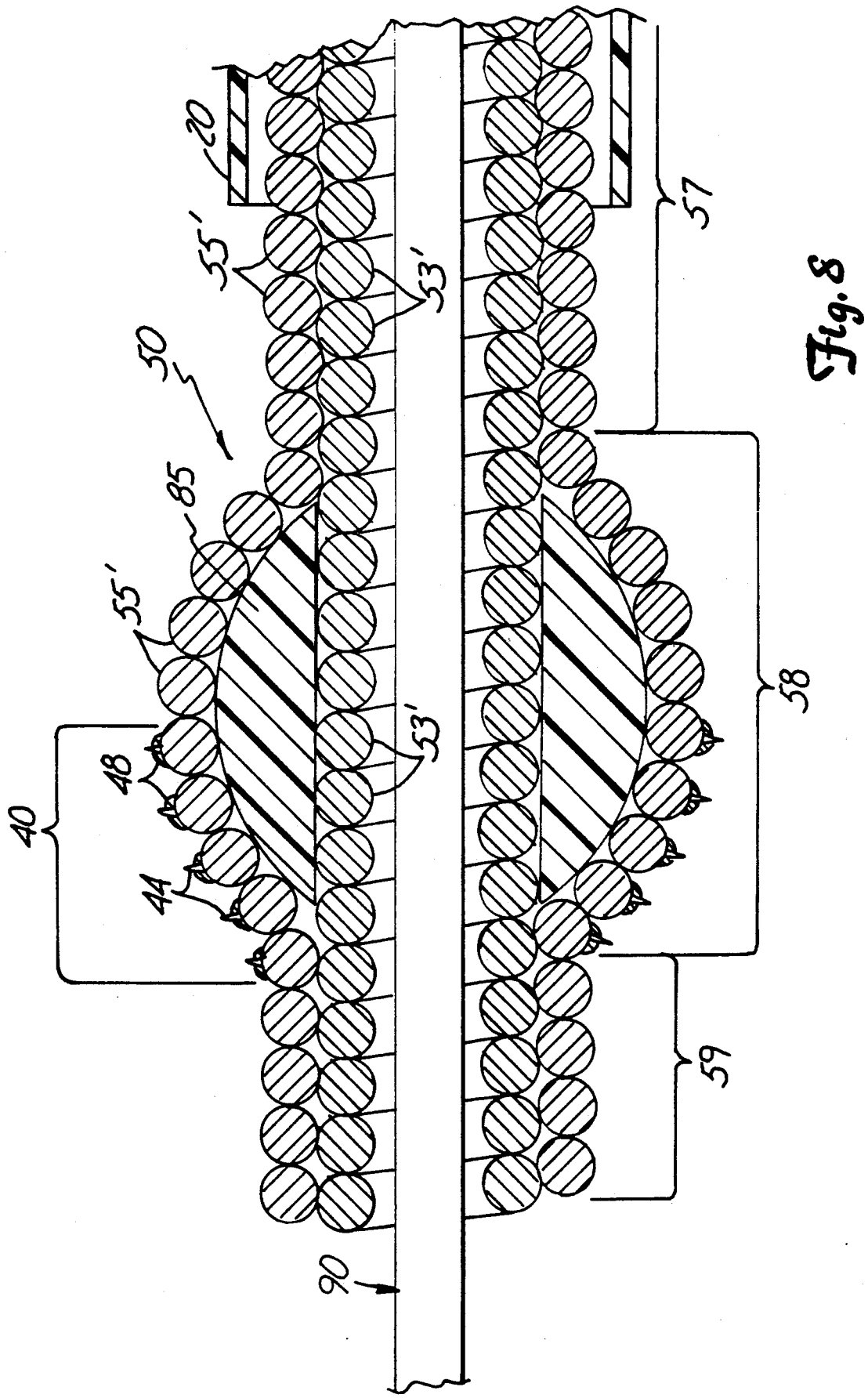
FIG. 8 depicts another modified embodiment similar to FIG. 3 but with the drive shaft having two helically wound layers, the inner layer having a generally constant diameter throughout its length, and the outer layer having enlarged diameter wire turns which define the drive shaft's intermediate segment.

Although FIGS. 1-6 illustrate a single layer helically wound drive shaft 50 (which may be mono-filar but preferably is multi-filar), a multi-layer helically wound drive shaft may also be utilized, as depicted in FIGS. 7-8. In such a drive shaft 50 a second, outer coaxial layer (either mono-filar or, preferably, multi-filar) of helically wound wire is utilized. In the embodiment shown in FIG. 7, the outer layer 55 extends only throughout the proximal segment 57 of the drive shaft, terminating just proximal to the intermediate segment 58 of the drive shaft. The inner layer 52 continues for the full length of the drive shaft, expanding in diameter to define the intermediate segment 58 of the drive shaft.

In the embodiment shown in FIG. 8, the outer layer 55' extends for substantially the entire length of the drive shaft, expanding in diameter to define the intermediate segment 58 of the drive shaft. The inner layer 53' preferably does not expand in diameter in the intermediate segment, but has a substantially constant cross-sectional diameter throughout its length. In this embodiment a toroidal collar 85 may be provided to support the wire turns of the intermediate segment 58 of the outer layer 55'. This collar may be made of metal (e.g., stainless steel) or, preferably, suitable flexible plastics (e.g., TEFLON ®). Since the collar 85 is effectively encapsulated by the inner and outer wire layers 53' and 55', attachment of the collar to the drive shaft is not critical.

In both of the embodiments of FIGS. 7 and 8, typically the wire layers are helically wound in opposite directions so that upon application of torque to the proximal end of the drive shaft 50 (when the turbine or other rotational power source is actuated in a predetermined rotational direction) the outer wire layer 55 will tend to radially contract and the inner wire layer 52 will tend to radially expand, the two wire layers thus supporting one another and preventing a decrease of the inner diameter and an increase of the outer diameter of the drive shaft.

Although for ease of illustration the drawings depict the wire of both layers of the two-layer drive shaft 50 to be of the same diameter, in practice it may be desirable to make one of the layers from a wire having a slightly larger diameter than the other. For example, if one of the layers is made from 0.004" diameter wire, the other wire may desirably be made from 0.005" diameter wire.

Moreover, while the drawings depict the wire of the drive shaft 50 to be generally round in cross-section, it will be appreciated that wires of other shapes, such as flattened rectangular, oval, etc., could also be utilized. For example, use of flattened rectangular wire (typically with rounded corners) will provide each individual wire turn of the abrasive segment with more surface for the fixation of diamond particles to these individual wire turns, allowing one to maintain relatively small diameters of the proximal and distal segments of the drive shaft. Such flattened rectangular wire can be of any suitable dimensions. For example, wire having a cross-sectional height of about 0.002–0.008 inches, and a width of up to about three to five times the height may be utilized. Stainless steel wire of this type is commercially available from various sources, including the Wire Division of MicroDyne Technologies (New Britain, Conn.).

It will be appreciated that the representations in FIGS. 2-8 are somewhat schematic. In many of the views the abrasive particles 44 are shown as being attached in neat rows centered along the wire turns 52 of the drive shaft 50. Depending on the method of applying the abrasive particles 44, the particles more likely will be distributed somewhat randomly over the abrasive segment (or wire turns) of the drive shaft. Moreover, the relative size of the abrasive particles in relation to the diameter of the wire of the drive shaft coil may vary from one application to another. For example, in a typical coronary application (i.e., use in coronary arteries) round wire having a diameter of about 25-150 $\mu$m (and preferably of about 50-125 $\mu$m) may be wound into a drive shaft 50 having a proximal segment 57 with an outer diameter of about 0.2-1.5 mm (and preferably about 0.3-1.2 mm); the intermediate segment 58 of such a device desirably has a maximum outer diameter not more than about four times larger than the diameter of the proximal segment 57 (and preferably not more than about 2-3 times larger than the diameter of the proximal segment 57). Abrasive particles 44 in the range of about 5 $\mu$m to about 30 $\mu$m (and preferably from about 10 $\mu$m to about 25 $\mu$m) are secured to the wire turns 52 of the drive shaft 50 with a bonding material 48 having a thickness of from about 3 $\mu$m to about 15 $\mu$m. This thickness (3-15 $\mu$m) of bonding material represents only the thickness of that portion of the bonding material which may be located between the particles 44 and the wire turns 52 of the drive shaft 50. Thus, the "effective thickness" of the abrasive material, including both the abrasive particles 44 and the bonding material 48, may be in the range of about 8 $\mu$m to about 45 $\mu$m, and preferably in the range of about 15 $\mu$m to about 35 $\mu$m.

Both the single layer and the two-layer multistrand helically wound flexible drive shafts described above are preferably made from stainless steel wire and can be obtained from commercial sources such as Lake Region Manufacturing Inc. (Chaska, Minn.). Other suitable alloys may also be used.

In a procedure, utilizing the abrasive drive shaft of the invention to remove stenotic tissue from an artery, a guide wire 90 is first advanced through the artery to a position where its distal tip 96 is located distally of the stenosis. The catheter 20 and the flexible drive shaft 50 with its abrasive segment 40 are then advanced over the shaft 92 of the guide wire 90 to a position locating the abrasive segment 40 just proximal to the stenotic lesion 12.

At this point, the flexible drive shaft 50 with its abrasive segment 40 is rotated at relatively high speed and is advanced distally across the stenosis to initiate the removal of the stenotic lesion. The speed of rotation typically is in the range of about 30,000 RPM to about 600,000 RPM, or even more, depending only on the physical dimensions and capabilities of the turbine/motor and flexible drive shaft. Typically the procedure will begin with a drive shaft having an intermediate segment with a maximum cross-sectional diameter larger than the proximal segment of the drive shaft and larger than the vascular opening through the stenosis but smaller than the normal, healthy diameter of the artery. Once the abrasive segment of the drive shaft has been advanced and retracted through the stenosis to open the stenosis to a diameter equal to the maximum diameter of the intermediate segment of the drive shaft, the drive shaft and catheter can be removed and a drive shaft with a larger diameter intermediate segment can be reinserted over the guide wire to continue removing stenotic tissue. In a typical procedure devices with drive shafts of two or three progressively larger intermediate (abrasive) segment diameters may be utilized to open the artery to a diameter close to its original, healthy diameter.

Commercially available angioplasty equipment (e.g., arterial puncture needles, arterial dilators, sheath introducers and guide catheters) and routine angioplasty techniques are used to appropriately position and manipulate the abrasive drive shaft device in the above-described interventional procedure. The above-described procedure should also utilize conventional fluoroscopic imaging techniques (with or without radio-opaque contrast solution injections), and the longitudinal positioning of the device within the artery may be assisted by placing special radio-opaque markings on the elements of the device and/or preferably components of the device can themselves be manufactured from radio-opaque materials.

Figure 9:
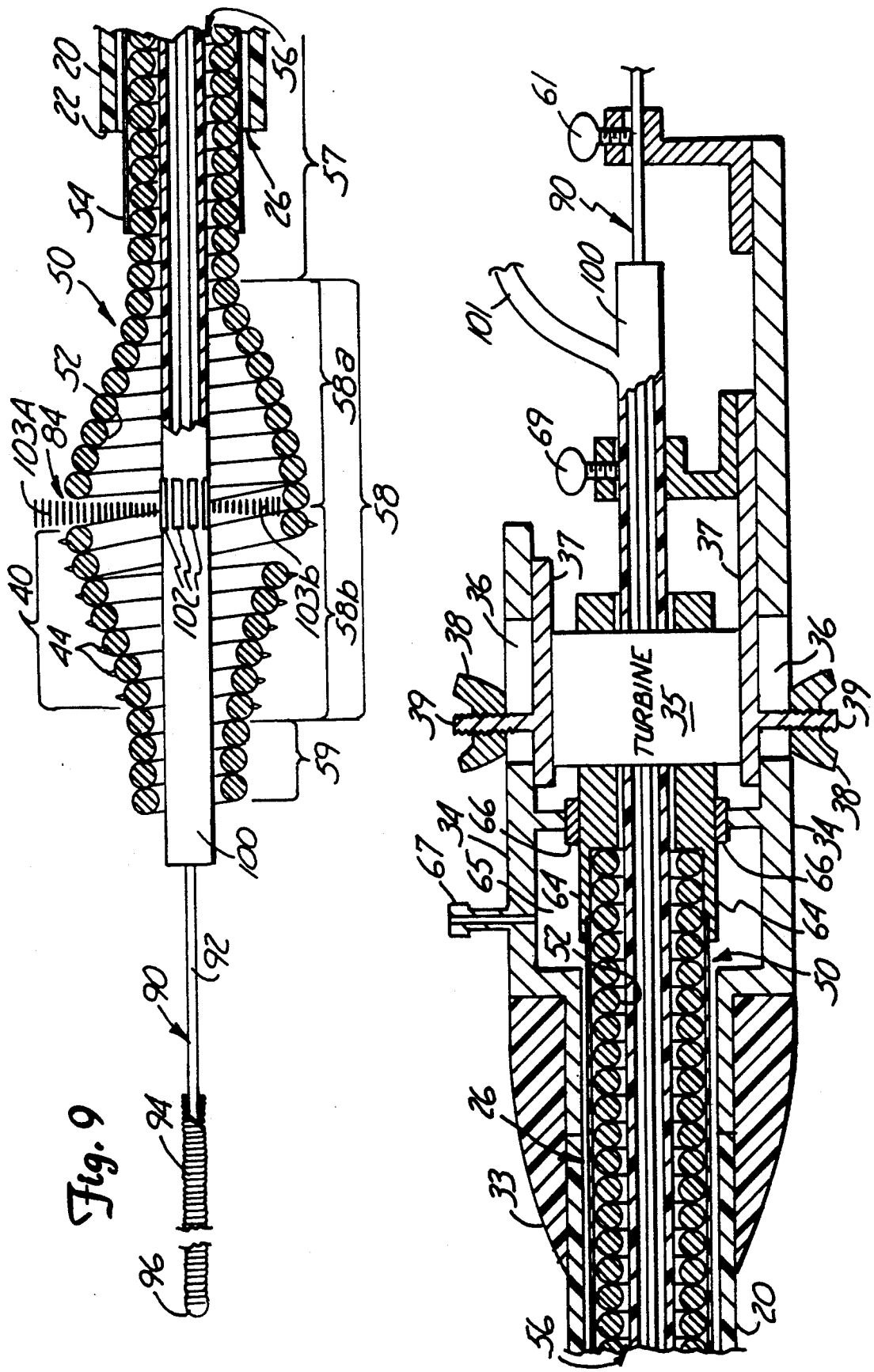
FIG. 9 is a partially broken away view of another embodiment of the invention, similar to FIG. 1, with the addition of an intravascular ultrasound imaging catheter positioned over the guide wire inside the lumen of the abrasive drive shaft, the abrasive drive shaft being rotatable over the ultrasound catheter.

FIGS. 9-22 illustrate an alternate embodiment of the invention in which an intravascular ultrasonic imaging probe (imaging catheter) 100 is utilized to image, in real time, the removal of stenotic tissue from the artery (or other body passageway). In this embodiment (referring now to FIG. 9), an ultrasonic catheter 100 is advanced over the guide wire 90 within the lumen 56 of the flexible drive shaft 50 to a position locating the catheter's ultrasound transducer elements 102 in alignment with an opening or gap 84 in the wire turns 52 of the intermediate segment 58 of the drive shaft 50. The proximal end portion of the ultrasound imaging catheter 100 may be selectively secured to the housing 34 by a suitable set screw 69 (or equivalent mechanism), so that the longitudinal position of the ultrasound imaging catheter with respect to the drive shaft 50 can be adjusted and then secured. Electrical connection of the ultrasonic imaging catheter 100 to the ultrasound machine (not shown) is made by cable 101. If necessary, a special port may be provided in the proximal portion of the ultrasound imaging catheter 100 for infusing lubricating fluid (such as saline or glucose solutions and the like) around the guide wire 90.

The ultrasound transducers elements 102 emit ultrasonic waves 103. Waves 103$a$ emitted by ultrasonic transducers which are acoustically aligned with the opening or gap 84 will pass through that gap 84, and be reflected by the surrounding tissue, thereby providing data for generation of a visual image of such tissue. Waves 103$b$ emitted by ultrasonic transducers which are aligned across from the wire turns 52 of the abrasive drive shaft 50 will be reflected by the wire.

Figure 10:
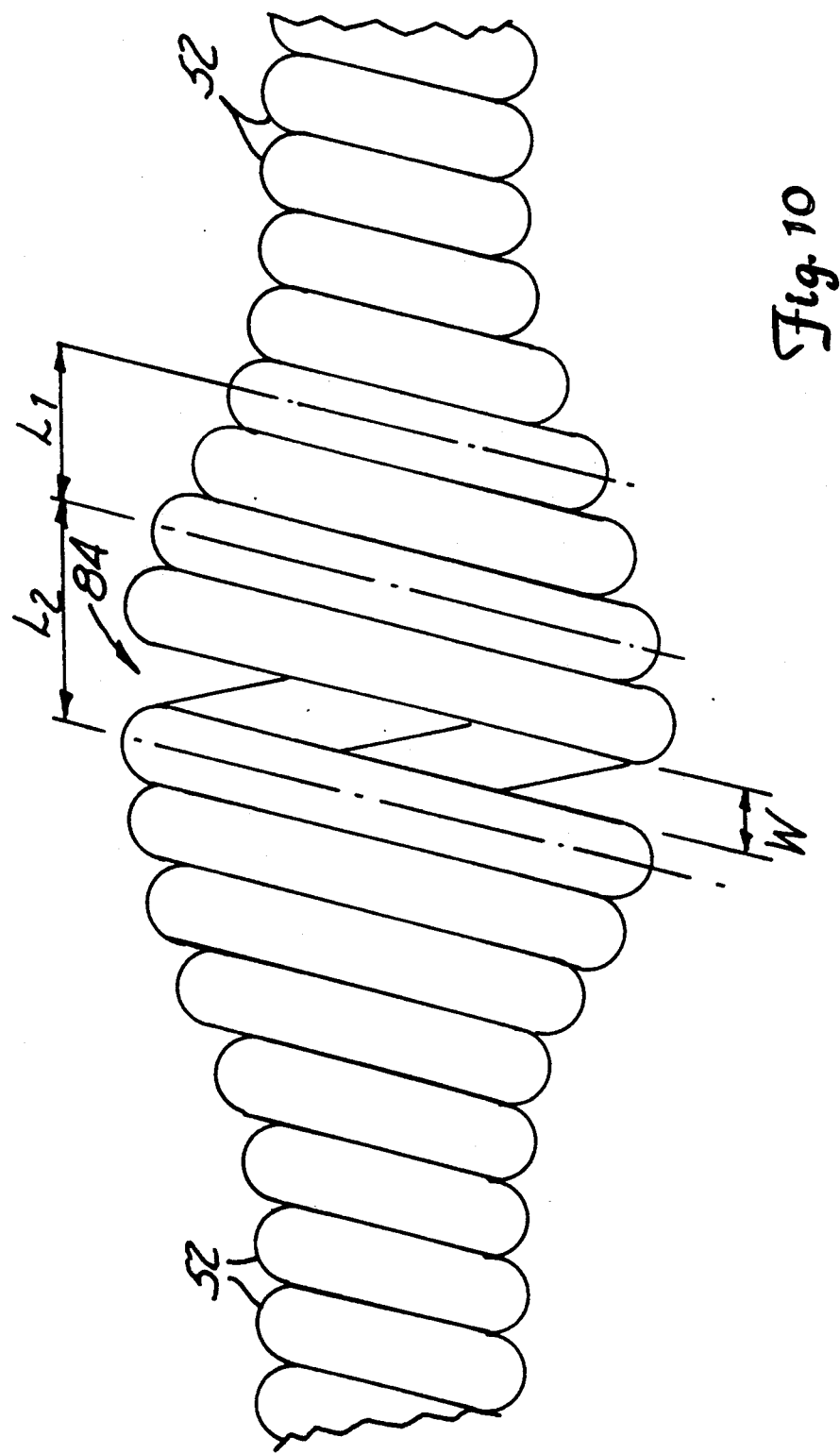
FIG. 10 is an enlarged view of a portion of the abrasive drive shaft of FIG. 8 (abrasive material not shown), illustrating the gap formed by temporarily changing the pitch of the wire turns of the intermediate segment of the drive shaft.
Figure 11:
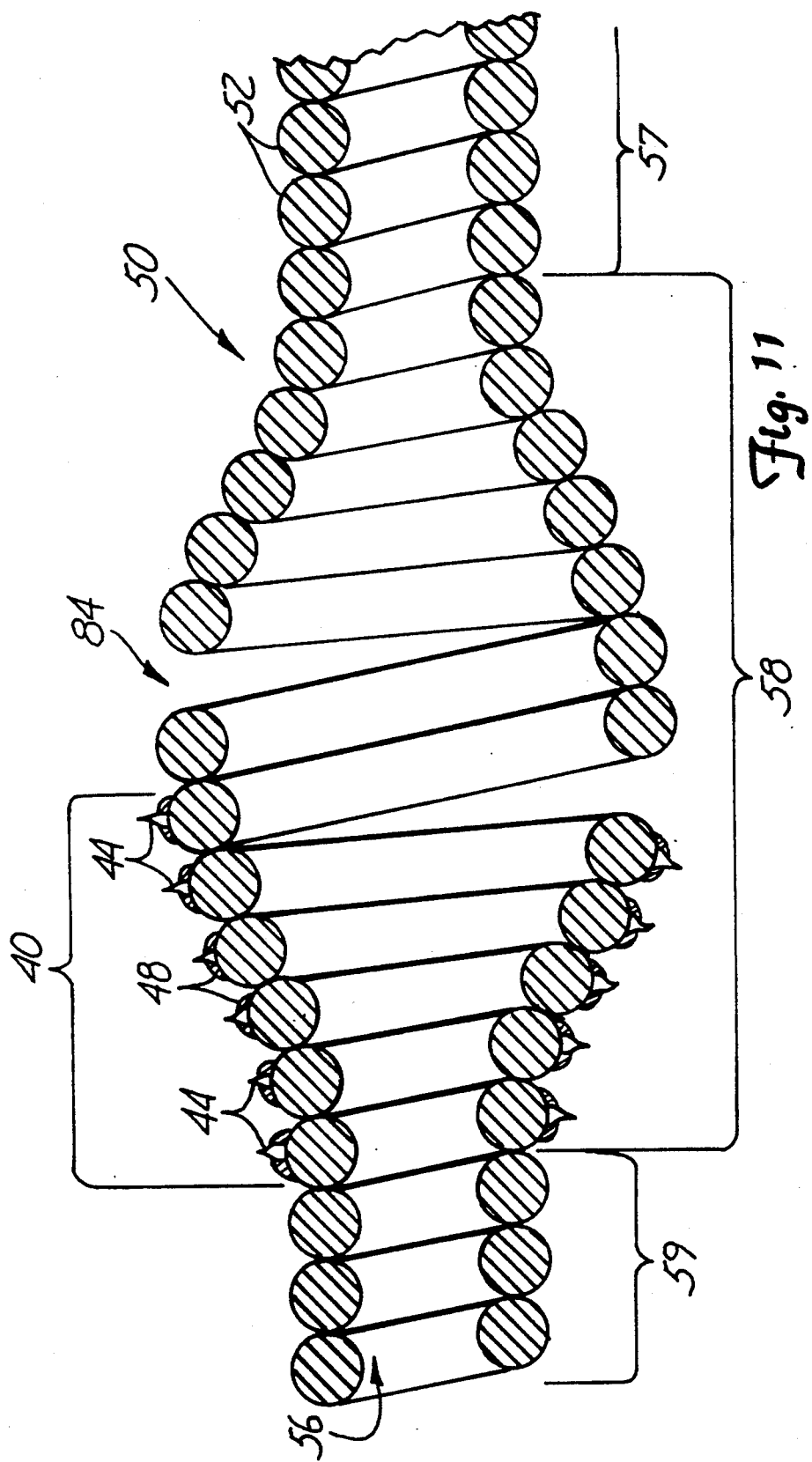
FIG. 11 is a longitudinal cross sectional view of FIG. 10, differing from FIG. 10 in that abrasive material (shown somewhat schematically) is shown attached to the turns of the wire of the abrasive segment of the drive shaft.

As illustrated in FIGS. 10 and 11, this gap 84 in the wire turns 52 of the drive shaft's intermediate segment 52 may be formed by providing the wire turns 52 of a short portion (typically about one turn) of the intermediate segment 58 with a pitch $L_2$ that is larger than the pitch $L_1$ of the wire turns of the intermediate segment 58 just proximal and distal to this short portion. This temporary change in pitch forms a gap 84 (having a width "W") between adjacent bi-filar turns of the drive shaft coil. Although the drawings depict the temporary transition from pitch $L_1$ to pitch $L_2$ in the center of the intermediate segment 58 of the drive shaft 50, it may be located at any convenient portion of the drive shaft—locating it close to or in the abrasive segment 40 provides what is likely to be the most useful image (i.e., at the point where stenotic tissue is being removed).

Moreover, if the gap 84 (and consequently the ultrasound transducers 102 of the ultrasound catheter 100) is located at the point of greatest diameter of the intermediate segment 58 of the drive shaft 50, the physician will be able to monitor the thickness of the stenotic tissue at this point of maximum diameter, and will be able to more accurately determine whether additional stenotic tissue can be removed without substantially increasing the risk of perforation of the artery wall.

For clarity, the abrasive material bonded to the turns of the drive shaft 50 is not shown in FIG. 10—FIG. 11 is a longitudinal cross sectional view of FIG. 10 differing from FIG. 10 in that abrasive material (shown somewhat schematically) is depicted on the turns of the wire of the abrasive segment of the drive shaft. Notice that the larger pitch $L_2$ need extend for only about one turn of the wire to create the desired gap.

Figure 12:
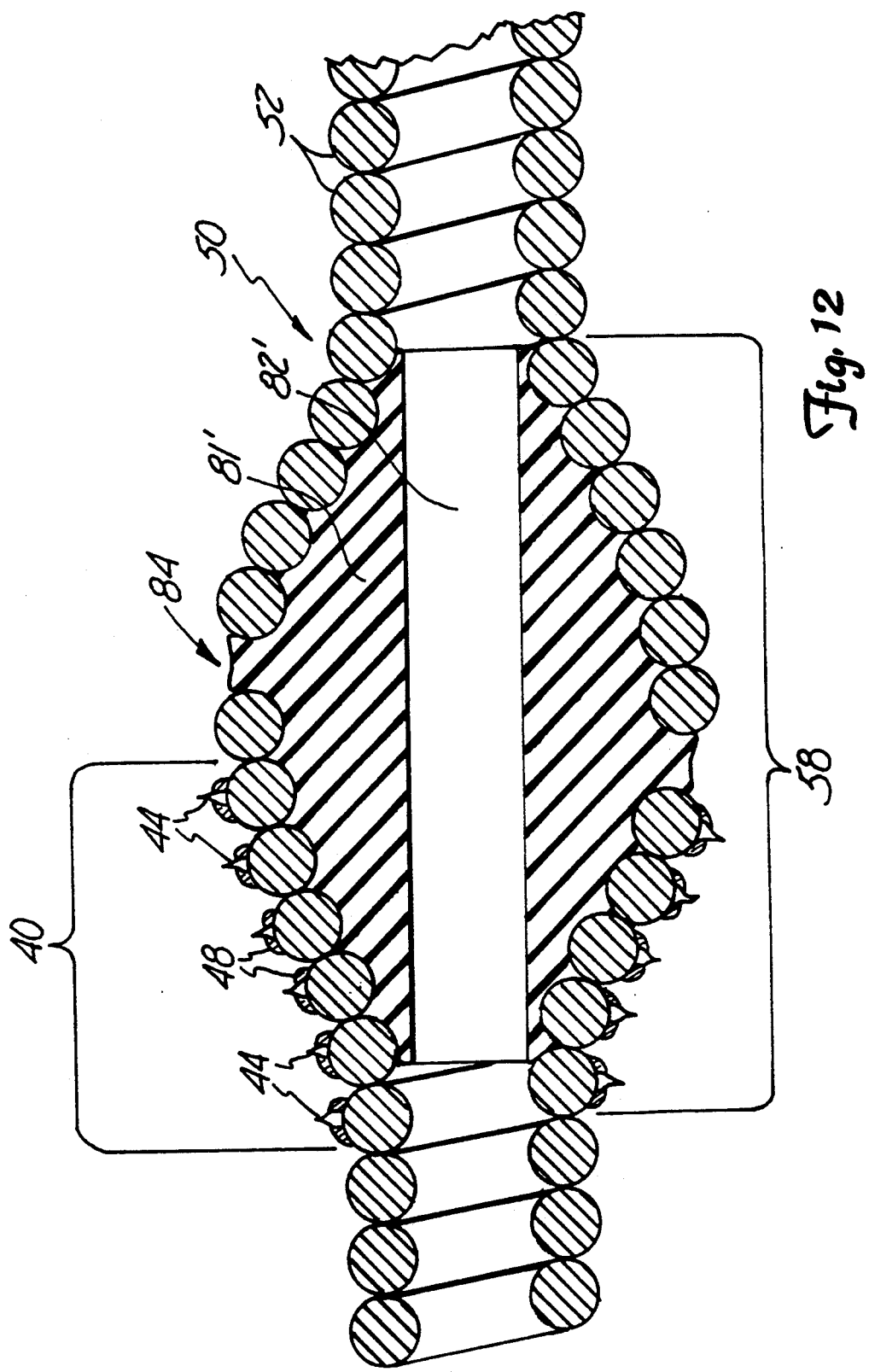
FIG. 12 is a view similar to FIG. 11 depicting a sonolucent bushing supporting the enlarged diameter wire turns of the intermediate segment of the drive shaft.
Figure 13:
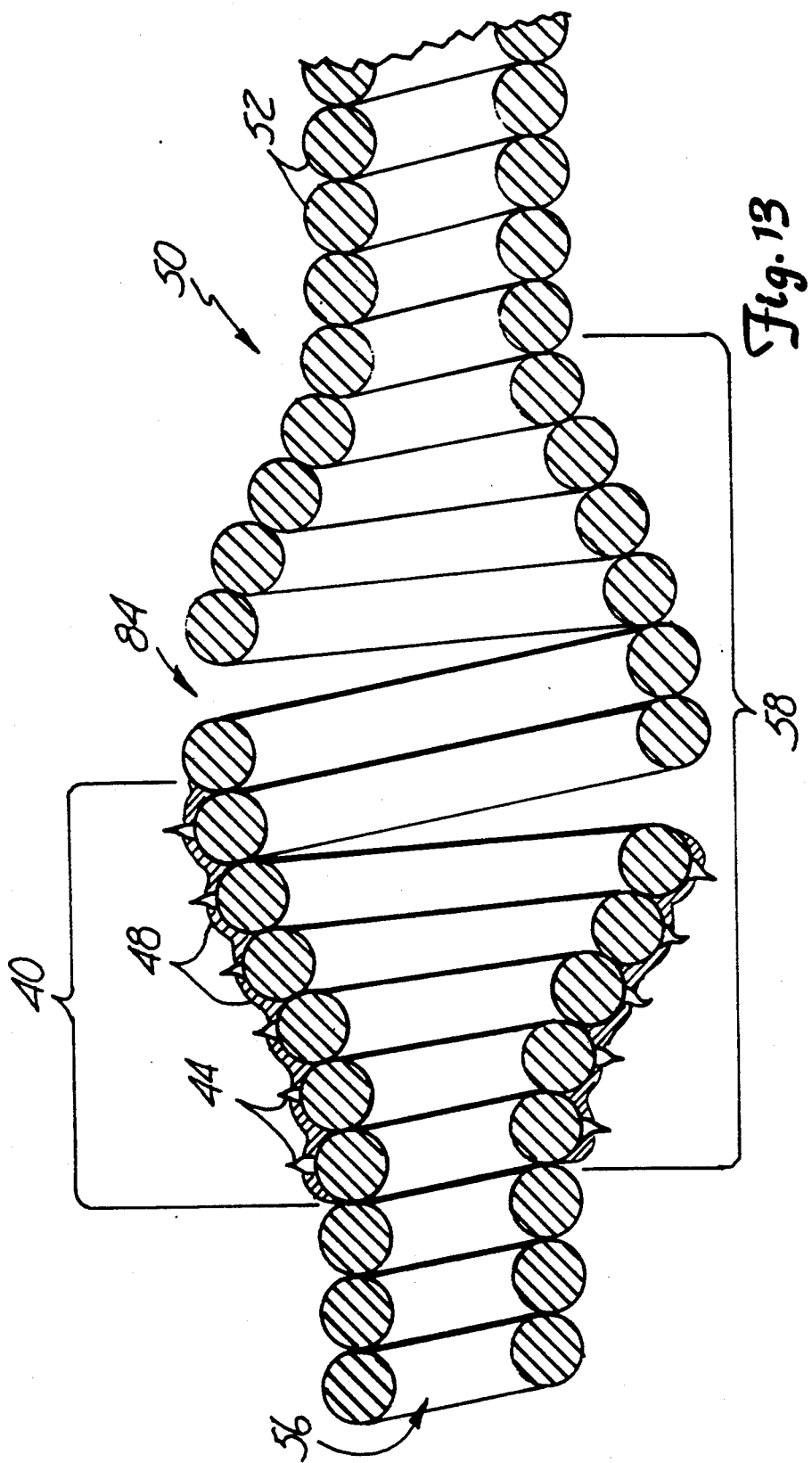
FIG. 13 shows another embodiment similar to FIG. 11 with bonding material not only attaching the abrasive material to the turns of the wire of the abrasive segment but also securing to one another the adjacent wire turns of the abrasive segment of the drive shaft.

FIGS. 12 and 13 illustrate additional embodiments of a drive shaft with an ultrasonic window or gap in the intermediate segment of the drive shaft. In FIG. 12 the intermediate segment 58 is provided with a bushing 81' (similar to FIG. 3). The bushing 81' of FIGS. 12, 14-16, 19, 21 and 22 differs from the bushing 81 of FIG. 3 in that it is sonolucent (i.e., relatively transparent to ultrasound waves, minimally reflecting or attenuating ultrasonic energy). Materials such as silicone, latex as well as certain plastics (e.g., polyethylene) are suitable for such a sonolucent bushing 81'. Desirably at least the surface of the bushing lumen 82' is made of (or coated with) a low friction, sonolucent material to reduce friction against the outer surface of the ultrasonic catheter 100 as the drive shaft 50 and bushing 81' rotate around the ultrasound catheter.

In FIG. 12 the bonding material 48 (which attaches the abrasive particles 44 to the wire turns 52 of the abrasive segment 40) is applied so as not to bond adjacent wire turns 52 to one another, thus preserving (to the extent permitted by the flexibility of the bushing 81') the flexibility of the abrasive segment 40. In FIG. 13 the bonding material 48 is applied continuously over the abrasive segment 40 to secure adjacent wire turns 52 to one another, thus making the abrasive segment 40 generally inflexible.

Figure 14:
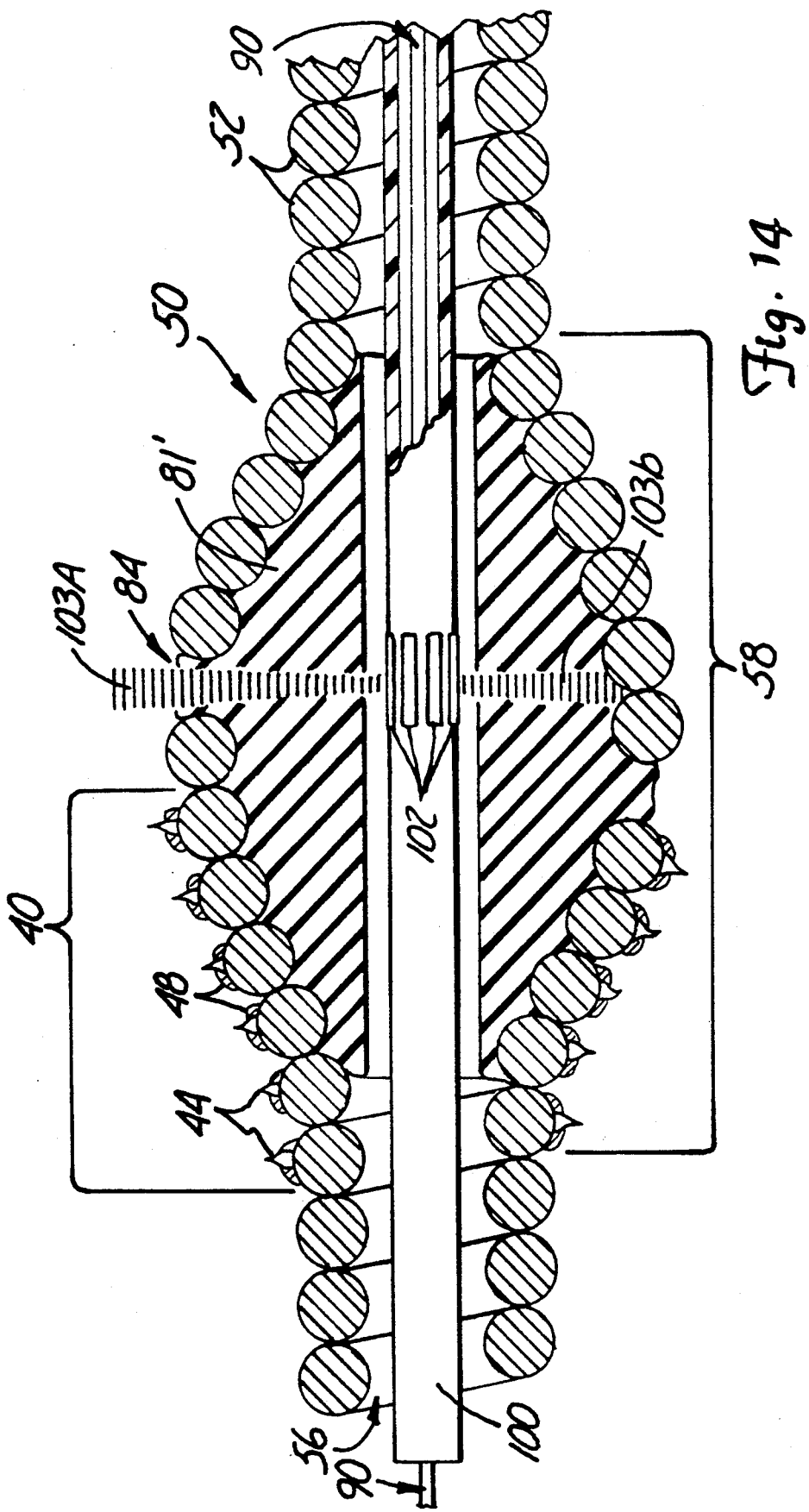
FIG. 14 is an enlarged view of a distal portion of the device of the invention shown in FIG. 9, the ultrasound catheter carrying a multi-element transducer array.

As illustrated in FIG. 14, an intravascular ultrasound imaging catheter 100 may be advanced over the guide wire 90 through the lumen 56 of the abrasive drive shaft 50 to a position where the transducer elements 102 (depicted schematically) of the ultrasound catheter 100 become acoustically aligned with the ultrasound window or gap 84 in the wire turns 52 of the intermediate segment 58 of the abrasive drive shaft 50 for use in ultrasonic imaging during the removal of the stenotic tissue. In this position the ultrasound catheter 100 will permit imaging of the relative cross-sectional position of the abrasive segment 40 of the drive shaft 50 with respect to the stenotic tissue, and imaging of the stenotic tissue as it is being removed.

FIGS. 15-18 illustrate both the utility of this imaging technique and the cross-sectional ultrasonic image of the artery through the gap or sonolucent window 84 between wire turns 52 of the abrasive segment. FIG. 15 shows, in longitudinal cross section, an artery 10 with an eccentric atherosclerotic lesion 12 partially obstructing blood flow in an artery 10. The abrasive drive shaft device of the invention together with the ultrasonic imaging catheter 100 has been partially advanced across the stenosis and has removed the proximal portion of an inner layer of atherosclerotic plaque 12. The ultrasound imaging elements 102 of the intravascular ultrasound imaging catheter 100 have been longitudinally aligned with the ultrasonic window 84 in the intermediate segment 58 of the abrasive drive shaft 50. FIG. 16 shows in transverse cross-section the alignment of these components.

Ultrasonic waves 103a, generated by the ultrasonic transducer elements 102 positioned across from the ultrasonic window 84, pass through the ultrasonic window 84 and are reflected by surrounding tissues (atherosclerotic tissue 12 and the wall of the artery 10). The ultrasonic waves 103b generated by the ultrasound transducers 102 positioned across from the metallic wire turns 52 are totally reflected by those wire turns 52, producing a bright line 52' of ultrasound echoes on the instantaneous cross-sectional ultrasound image depicted in FIG. 17.

FIG. 17 illustrates the expected instantaneous cross-sectional ultrasound image generated by the intravascular ultrasound imaging catheter 100. As discussed above, ultrasonic waves 103a, generated by the ultrasonic transducer elements 102 positioned across from the ultrasonic window 84, pass through the ultrasonic window 84 and are reflected by atherosclerotic tissue 12 and the wall of the artery 10, producing cross-sectional ultrasonic images of the plaque 12' and of the wall of the artery 10'. At the same time, the ultrasonic waves 103b which encounter the wire turns 52 of the abrasive drive shaft 50 will be completely reflected from the metallic wire and will produce only a bright line 52' of strong ultrasonic echoes corresponding to the surface of these metallic wires 52 with "black" shadow 109 outward of this bright line of echoes 52'.

The rotation of the drive shaft 50 and, hence, the ultrasonic window around the ultrasonic catheter 100, allows electronic reconstruction of a complete cross-sectional ultrasonic image of the artery shown on FIG. 18. This reconstructed ultrasonic image shows the depth of the atherosclerotic lesion 12'', the walls of the artery 10'' and, in general, the location of the abrasive drive shaft with respect to stenotic tissue and the wall of the artery. Viewing the ultrasound image, therefore, permits accurate selection of the diameter of the abrasive segment 40 for maximum removal of atherosclerotic tissue from within the artery, for continuous monitoring of the stenotic lesion removal throughout the procedure and thus allows removal of more of the stenotic lesion without significantly increasing the risk of perforation.

Two variations of the procedural techniques for utilizing the abrasive drive shaft device of the invention are as follows.

When, after injecting radiographic contrast into the stenotic artery (and imaging the stenosis fluoroscopically), a physician is still not sure whether the abrasive drive shaft atherectomy device of the invention is suitable for treatment of a stenosis, then, prior to advancing the abrasive drive shaft 50 across the stenosis 12, physician may advance the intravascular ultrasonic imaging catheter 100 over the guide wire 90 ahead of the abrasive drive shaft to "scout" the area of the stenosis. This enables the physician to further evaluate whether the device of the invention is likely to be effective in removing the stenotic tissue, to further assess the severity of the lesion in the artery, to better determine whether the lesion is calcified, whether it is eccentric or symmetrical, and to better determine the appropriate diameter of the abrasive drive shaft (i.e., the diameter of the intermediate segment of the drive shaft) which should be utilized to initiate the opening of the stenosis. At this time the entire strategy for the opening of the stenosis can be determined, including such things as which diameter abrasive drive shafts should be used, and in what sequence, to remove as much of the stenosis as possible, as efficiently as possible, and as safely as possible.

When, on the other hand (after injecting the radiographic contrast into the stenotic artery), the physician has determined that the stenotic lesion is of the type that can be successfully treated with the device of the invention, then the physician can advance the ultrasonic catheter 100 and the abrasive drive shaft 50 into the artery as a unit, stopping just proximal to the stenosis. The ultrasound catheter 100 can then be advanced to image the area to be treated, and then withdrawn to its position in the intermediate segment 58 of the drive shaft 50, and the entire unit can then be advanced to commence the stenosis removal procedure.

The above-described procedures for utilizing the device of the invention are only illustrative of the use of the invention, and a number of other procedural techniques may be utilized, as the physician deems appropriate.

FIG. 19 depicts a modified embodiment of the invention where, instead of an array of ultrasound transducers, the ultrasound catheter 100' is provided with two transducers 102', the ultrasound catheter being rotatable within the drive shaft 50 to produce the desired image. Typically the speed of rotation of the intravascular ultrasound imaging catheter 100' will be somewhat less than the speed of rotation of the drive shaft, and separate means is therefore provided proximally for rotating this ultrasound catheter.

FIG. 20 depicts another variation where a single ultrasonic transducer element 102" is provided on the ultrasound imaging catheter 100", and the catheter itself is attached to and rotates together with the drive shaft. The sonolucent bushing 81" in this embodiment is secured directly to both the wire turns 52 of the intermediate segment 58 of the drive shaft and the distal portion of the ultrasound imaging catheter 100", and thus does not actually function as a bushing, but supports the wire turns 52 of the intermediate segment 58. In this embodiment the ultrasonic transducer element is located in direct acoustic alignment with the gap in the wire turns of the drive shaft. Since the drive shaft may be rotated at speeds higher than may be desired for purposes of ultrasound imaging, in operation the speed of the drive shaft 50 may be periodically reduced to a lower speed selected for operation of the intravascular ultrasonic transducer 102".

FIG. 21 depicts yet another embodiment utilizing an intravascular ultrasound imaging catheter 100''' having a rotating acoustic reflector (acoustic mirror) 104 which radially redirects ultrasound imaging waves 103 (and returning echo waves) emitted (and received) by the non-rotating ultrasonic transducer 105. (An intravascular ultrasonic imaging probe utilizing an ultrasonic transducer and an acoustic reflector which are rotatable together as a unit inside the drive shaft may also be utilized.) The ultrasound imaging catheter 100''' is positioned longitudinally within the drive shaft 50 so that the acoustic reflector 104 is aligned with at least a portion of the gap or window 84 in the intermediate segment 58 of the drive shaft.

The above-described intravascular ultrasound imaging devices are generally commercially available, e.g., from Cardiovascular Imaging Systems, Inc. (Sunnyvale, Calif.), Boston Scientific Corp. (Watertown, Mass.), Endosonics, Inc. (Pleasanton, Calif.), and Intertherapy, Inc. (Santa Ana, Calif.). To the extent that ultrasonic imaging guide wires become commercially available, they could easily be used in lieu of the conventional guide wire and intravascular ultrasound imaging catheter depicted in the drawings.

Figure 22:
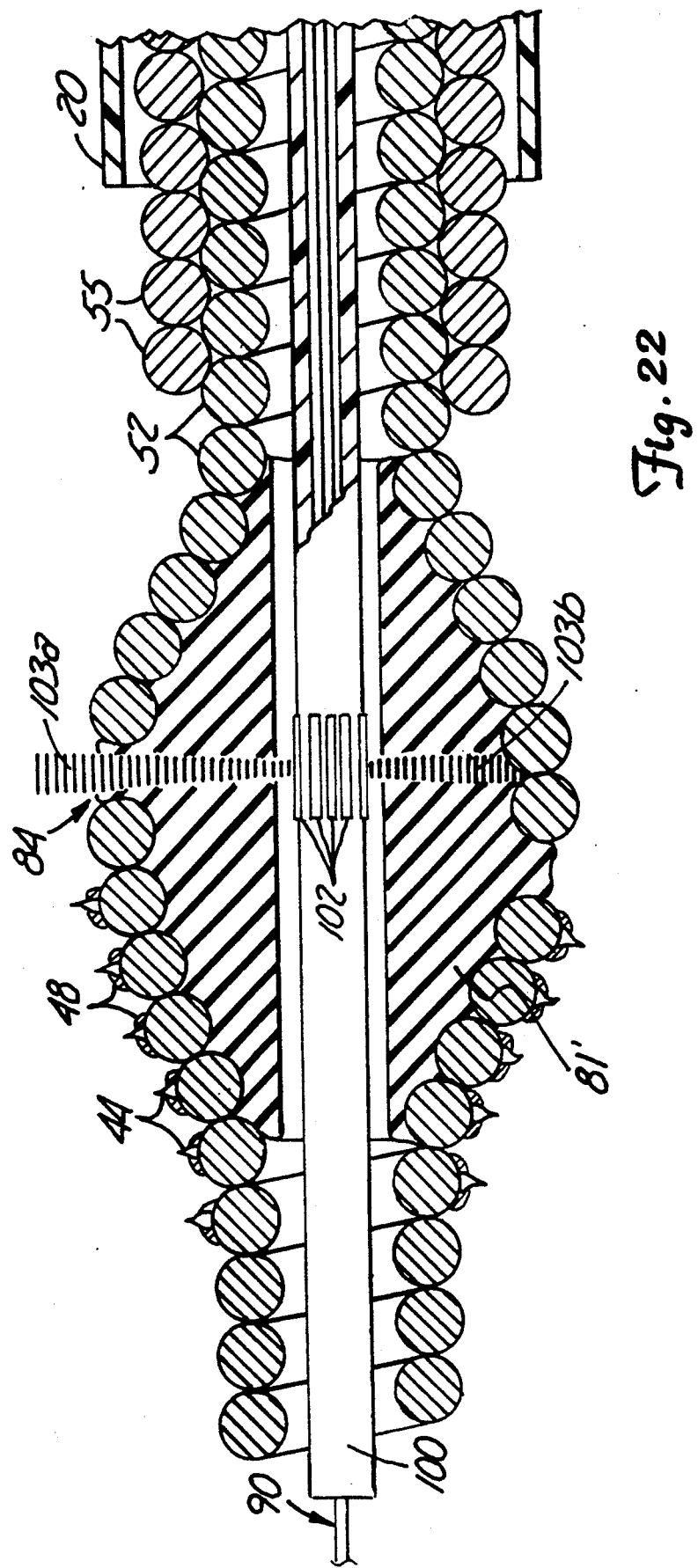
FIG. 22 shows another embodiment of the invention similar to FIG. 14, but with the drive shaft having two helically wound layers, the outer layer terminating just proximal to the intermediate segment of the drive shaft.

FIG. 22 illustrates yet a further variation of the device of the invention. This embodiment combines the two-layer drive shaft depicted in FIG. 7 with the intravascular ultrasound imaging techniques described above. Although the particular intravascular ultrasound imaging catheter 100 illustrated in this drawing is the array-type, any of the other types described above could also be utilized.

While a preferred embodiment of the present invention has been described, it should be understood that various changes, adaptations and modifications may be made therein without departing from the spirit of the invention and the scope of the appended claims.

What is claimed is:

1. An abrasive drive shaft atherectomy device comprising a flexible, elongated drive shaft having a central lumen for receipt of a guide wire therein around which the drive shaft may be rotated, the drive shaft being comprised of at least one helically wound wire and having proximal, intermediate and distal segments, wire turns of the proximal segment of the drive shaft having a generally constant diameter, turns of the intermediate segment of the drive shaft having a diameter that progressively increases distally through a proximal portion of such intermediate segment and having a diameter that progressively decreases distally through a distal portion of such intermediate segment, thereby defining an enlarged diameter segment of the drive shaft, at least part of the enlarged diameter intermediate segment including an external coating of an abrasive material to define an abrasive segment of the drive shaft, the intermediate segment of the drive shaft including a gap between adjacent wire turns to define a sonolucent window in the intermediate segment.

2. The abrasive drive shaft atherectomy device of claim 1 wherein the wire turns of the drive shaft in the distal portion of the intermediate segment progressively decrease distally in diameter to a diameter not larger than the diameter of the wire turns of the proximal segment of the drive shaft.

3. The abrasive drive shaft atherectomy device of claim 1 wherein the wire turns of the drive shaft's intermediate segment have a first pitch, at least one wire turn of the intermediate segment having a second, larger pitch to form the gap defining the sonolucent window in the intermediate segment.

4. The abrasive drive shaft atherectomy device of claim 1 wherein the gap is formed by a change in the pitch of the wire turns of the helically wound wire drive shaft.

5. The abrasive drive shaft atherectomy device of claim 1 wherein the gap in the intermediate segment of the drive shaft is located generally between the proximal and distal portions of the intermediate segment.

6. The abrasive drive shaft atherectomy device of claim 1 further comprising an intravascular ultrasonic imaging probe carrying ultrasonic imaging means for imaging tissue of interest, the probe being advanceable into the central lumen of the drive shaft to a position acoustically aligning the ultrasonic imaging means with the sonolucent window in the intermediate segment of the drive shaft, permitting acoustic signals generated by the ultrasonic imaging means to propagate through the sonolucent window.

7. The abrasive drive shaft atherectomy device of claim 6 wherein the ultrasonic imaging means includes an array of ultrasonic transducer elements.

8. The abrasive drive shaft atherectomy device of claim 6 wherein the abrasive drive shaft is rotatable with respect to the intravascular ultrasonic imaging probe.

9. The abrasive drive shaft atherectomy device of claim 6 wherein the ultrasonic imaging means is secured to the drive shaft for rotation together with the drive shaft.

10. The abrasive drive shaft atherectomy device of claim 6 wherein the ultrasonic imaging means comprises an ultrasonic transducer element and an acoustic reflector.

11. The abrasive drive shaft atherectomy device of claim 10 wherein the acoustic reflector is rotatable with respect to the ultrasonic transducer element.

12. The abrasive drive shaft atherectomy device of claim 10 wherein the acoustic reflector and the ultrasonic transducer element are rotatable together as a unit.

13. The abrasive drive shaft atherectomy device of claim 6 wherein the intravascular ultrasonic imaging probe comprises an intravascular ultrasonic imaging catheter.

14. The abrasive drive shaft atherectomy device of claim 6 wherein the intravascular ultrasonic imaging probe comprises an ultrasonic imaging guide wire.

15. The abrasive drive shaft atherectomy device of claim 1 wherein the intermediate segment of the drive shaft includes a gap between adjacent wire turns to define a window in the intermediate segment, the abrasive shaft atherectomy device further including imaging means, advancable into the central lumen of the drive shaft to a position aligning said imaging means with the window in the intermediate segment of the drive shaft, for imaging tissue surrounding the intermediate segment of the drive shaft.

16. The abrasive drive shaft atherectomy device of claim 1 further comprising a bushing disposed within the intermediate segment of the drive shaft, the bushing having an outer surface engaging and supporting the wire turns of at least a portion of the intermediate segment, and having an inner longitudinal bore therethrough, the bore being generally coaxial with the drive shaft lumen.

17. The abrasive drive shaft atherectomy device of claim 16 wherein the diameter of the bushing bore is sized to receive the guide wire therein.

18. The abrasive drive shaft atherectomy device of claim 16 wherein the bushing is made of a flexible material.

19. The abrasive drive shaft atherectomy device of claim 16 wherein the bushing is made of a sonolucent material.

20. The abrasive drive shaft atherectomy device of claim 19 wherein the sonolucent material is silicone.

21. The abrasive drive shaft atherectomy device of claim 16 wherein the bushing is made of a low friction material.

22. The abrasive drive shaft atherectomy device of claim 21 wherein the low friction material is polytetrafluoroethylene.

23. The abrasive drive shaft atherectomy device of claim 16 wherein the inner surface of the bushing bore is made of a low friction material.

24. The abrasive drive shaft atherectomy device of claim 1 further comprising a flexible, low friction sheath covering at least that portion of the drive shaft immediately proximal to the intermediate segment of the drive shaft.

25. The abrasive drive shaft atherectomy device of claim 24 wherein the sheath is made of polytetrafluoroethylene.

26. The abrasive drive shaft atherectomy device of claim 24 further comprising a low friction sheath covering the distal segment of the drive shaft.

27. The abrasive drive shaft atherectomy device of claim 1 further comprising a flexible, low friction coating covering at least that portion of the drive shaft immediately proximal to the intermediate segment of the drive shaft.

28. The abrasive drive shaft atherectomy device of claim 27 wherein the coating is made of polytetrafluoroethylene.

29. The abrasive drive shaft atherectomy device of claim 1 wherein the drive shaft is made from wire substantially completely coated with polytetrafluoroethylene.

30. The abrasive drive shaft atherectomy device of claim 1 wherein the abrasive material comprises a plurality of abrasive particles which are secured directly to the wire turns of the drive shaft by a bonding material.

31. The abrasive drive shaft atherectomy device of claim 1 wherein the abrasive material comprises a plurality of abrasive particles which are secured directly to the drive shaft by a bonding material.

32. The abrasive drive shaft atherectomy device of claim 30 wherein the bonding material is applied to adjacent turns of the helically wound wire to secure the abrasive material to such turns and to secure at least some of such adjacent turns to one another.

33. The abrasive drive shaft atherectomy device of claim 30 wherein the bonding material is applied to adjacent turns of the helically wound wire to secure abrasive material to such turns without securing any of such adjacent turns to one another.

34. The abrasive drive shaft atherectomy device of claim 31 wherein the abrasive particles are at least partially embedded in the bonding material, the thickness of the bonding material between substantially all of the abrasive particles and the drive shaft being not more than about 15 $\mu$m.

35. The abrasive drive shaft atherectomy device of claim 31 wherein the abrasive particles are at least partially embedded in the bonding material, the thickness of the bonding material between substantially all of the abrasive particles and the drive shaft being not more than about 5 $\mu$m.

36. The abrasive drive shaft atherectomy device of claim 1 wherein the abrasive material comprises diamond chips having a largest dimension of substantially 30 $\mu$m or less.

37. The abrasive drive shaft atherectomy device of claim 1 wherein the abrasive material comprises diamond chips having a largest dimension of substantially 25 $\mu$m or less.

38. The abrasive drive shaft atherectomy device of claim 1 wherein the coating of abrasive material is not thicker than about 45 $\mu$m.

39. The abrasive drive shaft atherectomy device of claim 1 wherein the coating of abrasive material is not thicker than about 35 μm.

40. The abrasive drive shaft atherectomy device of claim 1 wherein the maximum diameter of the abrasive segment, including the thickness of the abrasive coating, is not more than about 90 μm larger than the maximum outer diameter of the wire turns of the abrasive segment of the drive shaft.

41. The abrasive drive shaft atherectomy device of claim 1 wherein the maximum diameter of the abrasive segment, including the thickness of the abrasive coating, is not more than about 70 μm larger than the maximum outer diameter of the wire turns of the abrasive segment of the drive shaft.

42. The abrasive drive shaft atherectomy device of claim 1 wherein the coating of abrasive material is of a generally uniform thickness throughout the length of the abrasive segment.

43. The abrasive drive shaft atherectomy device of claim 1 wherein the drive shaft comprises a plurality of helically wound wires.

44. The abrasive drive shaft atherectomy device of claim 1 wherein the drive shaft is comprised of inner and outer co-axial wire layers helically wound in opposite directions to that the outer layer tends to radially contract and the inner layer tends to radially expand when the drive shaft is rotated in a predetermined direction.

45. The abrasive drive shaft atherectomy device of claim 44 wherein the outer wire layer extends along substantially the entire proximal segment of the drive shaft and terminates just proximal to the intermediate segment of the drive shaft.

46. The abrasive drive shaft atherectomy device of claim 44 wherein the outer wire layer extends along substantially all of the proximal and intermediate segments, and at least partially along the distal segment of the drive shaft.

47. An abrasive drive shaft atherectomy device comprising a flexible, elongated drive shaft having a central lumen for receipt of a guide wire therein around which the drive shaft may be rotated, the drive shaft being comprised of at least one helically wound wire and having proximal, intermediate and distal segments, wire turns of the proximal segment of the drive shaft having a generally constant diameter, turns of the intermediate segment of the drive shaft having a diameter that progressively increases distally through a proximal portion of such intermediate segment and having a diameter that progressively decreases distally through a distal portion of such intermediate segment to a diameter not larger than the diameter of the proximally segment of the drive shaft, thereby defining an enlarged diameter segment of the drive shaft, at least part of the enlarged diameter intermediate segment including an external coating of diamond chips secured directly to the drive shaft wire by a bonding material to define an abrasive segment of the drive shaft, the coating of diamond chips being of a generally uniform thickness throughout the length of the abrasive segment and the thickness of the bonding material between substantially all of the diamond chips and the drive shaft being not more than about 15 μm, the atherectomy device further including a bushing disposed within the intermediate segment of the drive shaft, the bushing having an outer surface engaging and supporting the wire turns of at least the central portion of the intermediate segment, the bushing having an inner longitudinal bore therethrough which is generally coaxial with the drive shaft lumen, the bushing bore having a low friction inner surface and being sized to receive the guide wire therein.

48. The abrasive drive shaft atherectomy device of claim 47 wherein the bushing is sonolucent, and the intermediate segment of the drive shaft includes a gap between adjacent wire turns to define a sonolucent window located generally between the proximal and distal portions of the intermediate segment of the drive shaft, the abrasive drive shaft atherectomy device further including an intravascular ultrasonic imaging probe carrying ultrasonic imaging means for imaging tissue of interest, the probe being advancable into the central lumen of the drive shaft to a position acoustically aligning the ultrasonic imaging means within the sonolucent window in the intermediate segment of the drive shaft, permitting acoustic signals generated by the ultrasonic imaging means to propagate through the sonolucent window.

49. An abrasive drive shaft atherectomy device comprising a flexible, elongated drive shaft having a central lumen for receipt of a guide wire therein around which the drive shaft may be rotated, the drive shaft being comprised of at least one helically wound wire and having proximal, intermediate and distal segments, wire turns of the proximal segment of the drive shaft having a generally constant diameter, turns of the intermediate segment of the drive shaft having a diameter that progressively increases distally through a proximal portion of such intermediate segment and having a diameter that progressively decreases distally through a distal portion of such intermediate segment, thereby defining an enlarged diameter segment of the drive shaft, at least part of the enlarged diameter intermediate segment including an external coating of an abrasive material to define an abrasive segment of the drive shaft, the device further including a bushing disposed within the intermediate segment of the drive shaft, the bushing having an outer surface engaging and supporting the wire turns of at least a central portion of the intermediate segment, and having an inner longitudinal bore therethrough, the bore being generally coaxial with the drive shaft lumen.

50. The abrasive drive shaft atherectomy device of claim 49 wherein the wire turns of the drive shaft in the distal portion of the intermediate segment progressively decrease distally in diameter to a diameter not larger than the diameter of the wire turns of the proximal segment of the drive shaft.

51. The abrasive drive shaft atherectomy device of claim 49 wherein the intermediate segment of the drive shaft includes a gap between adjacent wire turns to define a sonolucent window in the intermediate segment.

52. The abrasive drive shaft atherectomy device of claim 51 wherein the turns of the drive shaft's intermediate segment have a first pitch, at least one wire turn of the intermediate segment having a second, larger pitch to form the gap defining the sonolucent window in the intermediate segment.

53. The abrasive drive shaft atherectomy device of claim 51 wherein the gap is formed by a change in the pitch of the wire turns of the helically wound wire drive shaft.

54. The abrasive drive shaft atherectomy device of claim 51 wherein the gap in the intermediate segment of the drive shaft is located generally between the proximal and distal portions of the intermediate segment.

55. The abrasive drive shaft atherectomy device of claim 51 further comprising an intravascular ultrasonic imaging probe carrying ultrasonic imaging means for imaging tissue of interest, the probe being advanceable into the central lumen of the drive shaft to a position acoustically aligning the ultrasonic imaging means with the sonolucent window in the intermediate segment of the drive shaft, permitting acoustic signals generated by the ultrasonic imaging means to propagate through the sonolucent window.

56. The abrasive drive shaft atherectomy device of claim 55 wherein the ultrasonic imaging means includes an array of ultrasonic transducer elements.

57. The abrasive drive shaft atherectomy device of claim 55 wherein the abrasive drive shaft is rotatable with respect to the intravascular ultrasonic imaging probe.

58. The abrasive drive shaft atherectomy device of claim 55 wherein the ultrasonic imaging means is secured to the drive shaft for rotation together with the drive shaft.

59. The abrasive drive shaft atherectomy device of claim 55 wherein the ultrasonic imaging means comprises an ultrasonic transducer element and an acoustic reflector.

60. The abrasive drive shaft atherectomy device of claim 59 wherein the acoustic reflector is rotatable with respect to the ultrasonic transducer element.

61. The abrasive drive shaft atherectomy device of claim 59 wherein the acoustic reflector and the ultrasonic transducer element are rotatable together as a unit.

62. The abrasive drive shaft atherectomy device of claim 55 wherein the intravascular ultrasonic imaging probe comprises an intravascular ultrasonic imaging catheter.

63. The abrasive drive shaft atherectomy device of claim 55 wherein the intravascular ultrasonic imaging probe comprises an ultrasonic imaging guide wire.

64. The abrasive drive shaft atherectomy device of claim 49 wherein the intermediate segment of the drive shaft includes a gap between adjacent wire turns to define a window in the intermediate segment, the abrasive drive shaft atherectomy device further including imaging means, advanceable into the central lumen of the drive shaft to a position aligning said imaging means with the window in the intermediate segment of the drive shaft, for imaging tissue surrounding the intermediate segment of the drive shaft.

65. The abrasive drive shaft atherectomy device of claim 49 wherein the diameter of the bushing bore is sized to receive the guide wire therein.

66. The abrasive drive shaft atherectomy device of claim 49 wherein the bushing is made of a flexible material.

67. The abrasive drive shaft atherectomy device of claim 49 wherein the bushing is made of a sonolucent material.

68. The abrasive drive shaft atherectomy device of claim 67 wherein the sonolucent material is silicone.

69. The abrasive drive shaft atherectomy device of claim 49 wherein the bushing is made of a low friction material.

70. The abrasive drive shaft atherectomy device of claim 69 wherein the low friction material is polytetrafluoroethylene.

71. The abrasive drive shaft atherectomy device of claim 49 wherein the inner surface of the bushing bore is made of a low friction material.

72. The abrasive drive shaft atherectomy device of claim 49 further comprising a flexible, low friction sheath covering at least that portion of the drive shaft immediately proximal to the intermediate segment of the drive shaft.

73. The abrasive drive shaft atherectomy device of claim 72 wherein the sheath is made of polytetrafluoroethylene.

74. The abrasive drive shaft atherectomy device of claim 72 further comprising a low friction sheath covering the distal segment of the drive shaft.

75. The abrasive drive shaft atherectomy device of claim 49 further comprising a flexible, low friction coating covering at least that portion of the drive shaft immediately proximal to the intermediate segment of the drive shaft.

76. The abrasive drive shaft atherectomy device of claim 75 wherein the coating is made of polytetrafluoroethylene.

77. The abrasive drive shaft atherectomy device of claim 49 wherein the drive shaft is made from wire substantially completely coated with polytetrafluoroethylene.

78. The abrasive drive shaft atherectomy device of claim 49 wherein the abrasive material comprises a plurality of abrasive particles which are secured directly to the wire turns of the drive shaft by a bonding material.

79. The abrasive drive shaft atherectomy device of claim 49 wherein the abrasive material comprises a plurality of abrasive particles which are secured directly to the drive shaft by a bonding material.

80. The abrasive drive shaft atherectomy device of claim 78 wherein the bonding material is applied to adjacent turns of the helically wound wire to secure the abrasive material to such turns and to secure at least some of such adjacent turns to one another.

81. The abrasive drive shaft atherectomy device of claim 78 wherein the bonding material is applied to adjacent turns of the helically wound wire to secure the abrasive material to such turns without securing any of such adjacent turns to one another.

82. The abrasive drive shaft atherectomy device of claim 49 wherein the abrasive material comprises diamond chips having a largest dimension of substantially 30 μm or less.

83. The abrasive drive shaft atherectomy device of claim 49 wherein the coating of abrasive material is not thicker than about 48 μm.

84. The abrasive drive shaft atherectomy device of claim 49 wherein the maximum diameter of the abrasive segment, including the thickness of the abrasive coating, is not more than about 90 μm larger than the maximum outer diameter of the wire turns of the abrasive segment of the drive shaft.

85. The abrasive drive shaft atherectomy device of claim 49 wherein the coating of abrasive material is of a generally uniform thickness throughout the length of the abrasive segment.

86. The abrasive drive shaft atherectomy device of claim 49 wherein the drive shaft comprises a plurality of helically wound wires.

87. The abrasive drive shaft atherectomy device of claim 49 wherein the drive shaft is comprised of inner and outer co-axial wire layers helically wound in opposite directions so that the outer layer tends to radially contract and the inner layer tends to radially expand when the drive haft is rotated in a predetermined direction.

88. The abrasive drive shaft atherectomy device of claim 87 wherein the outer wire layer extends along substantially the entire proximal segment of the drive shaft and terminates just proximal to the intermediate segment of the drive shaft.

89. The abrasive drive shaft atherectomy device of claim 87 wherein the outer wire layer extends along substantially all of the proximal and intermediate segments, and at least partially along the distal segment of the drive shaft.

90. An abrasive drive shaft atherectomy device comprising a flexible, elongated drive shaft having a central lumen for receipt of a guide wire therein around which the drive shaft may be rotated, the drive shaft being comprised of inner and outer co-axial wire layers helically wound in opposite directions so that the outer layer tends to radially contract and the inner layer tends to radially expand when the rive shaft is rotated in a predetermined direction, the drive shaft having proximal, intermediate and distal segments, wire turns of the proximal segment of the drive shaft having a generally constant diameter, wire turns of the outer layer of the intermediate segment of the drive shaft having a diameter that progressively increases distally through a proximal portion of such intermediate segment and having a diameter that progressively decreases distally through a distal portion of such intermediate segment, thereby defining an enlarged diameter segment of the drive shaft, at least part of the enlarged diameter intermediate segment including an external coating of an abrasive material to define an abrasive segment of the drive shaft, and further including a generally toroidal collar positioned in the intermediate segment of the drive shaft between the inner and outer layers of the drive shaft.

91. The abrasive drive shaft atherectomy device of claim 90 wherein the wire turns of the outer layer of the drive shaft in the distal portion of the intermediate segment progressively decrease distally in diameter to a diameter not larger than the diameter of the wire turns of the outer layer of the proximal segment of the drive shaft.

92. The abrasive drive shaft atherectomy device of claim 90 wherein the collar is made of a flexible material.

93. The abrasive drive shaft atherectomy device of claim 90 wherein the collar is made of a metal.

94. The abrasive drive shaft atherectomy device of claim 90 wherein the collar is made of a plastic material.

95. The abrasive drive shaft atherectomy device of claim 90 further comprising a flexible, low friction sheath covering at least that portion of the drive shaft immediately proximal to the intermediate segment of the drive shaft.

96. The abrasive drive shaft atherectomy device of claim 95 wherein the sheath is made of polytetrafluoroethylene.

97. The abrasive drive shaft atherectomy device of claim 95 further comprising a low friction sheath covering the distal segment of the drive shaft.

98. The abrasive drive shaft atherectomy device of claim 90 further comprising a flexible, low friction coating covering at least that portion of the drive shaft immediately proximal to the intermediate segment of the drive shaft.

99. The abrasive drive shaft atherectomy device of claim 98 wherein the coating is made of polytetrafluoroethylene.

100. The abrasive drive shaft atherectomy device of claim 90 wherein the drive shaft is made from wire substantially completely coated with polytetrafluoroethylene.

101. The abrasive drive shaft atherectomy device of claim 90 wherein the abrasive material comprises a plurality of abrasive particles which are secured directly to the wire turns of the drive shaft by a bonding material.

102. The abrasive drive shaft atherectomy device of claim 90 wherein the abrasive material comprises a plurality of abrasive particles which are secured directly to the drive shaft by a bonding material.

103. The abrasive drive shaft atherectomy device of claim 101 wherein the bonding material is applied to adjacent turns of the helically wound wire to secure the abrasive material to such turns and to secure at least some of such adjacent turns to one another.

104. The abrasive drive shaft atherectomy device of claim 101 wherein the bonding material is applied to adjacent turns of the helically wound wire to secure the abrasive material to such turns without securing any of such adjacent turns to one another.

105. The abrasive drive shaft atherectomy device of claim 90 wherein the abrasive material comprises diamond chips having a largest dimension of substantially 30 $\mu$m or less.

106. The abrasive drive shaft atherectomy device of claim 90 wherein the coating of abrasive material is not thicker than about 45 $\mu$m.

107. The abrasive drive shaft atherectomy device of claim 90 wherein the maximum diameter of the abrasive segment, including the thickness of the abrasive coating, is not more than about 90 $\mu$m larger than the maximum outer diameter of the wire turns of the abrasive segment of the drive shaft.

108. The abrasive drive shaft atherectomy device of claim 90 wherein the coating of abrasive material is of a generally uniform thickness throughout the length of the abrasive segment.

109. The abrasive drive shaft atherectomy device of claim 90 wherein each layer of the drive shaft comprises a plurality of helically wound wires.

110. The abrasive drive shaft atherectomy device of claim 90 wherein the outer wire layer extends along substantially all of the proximal and intermediate segments, and at least partially along the distal segment of the drive shaft.

111. The abrasive drive shaft atherectomy device comprising a flexible, elongated drive shaft having a central lumen for receipt of a guide wire therein around which the drive shaft may be rotated, the drive shaft being comprised of at least two helically wound wires forming inner and outer co-axial wire layers helically wound in opposite directions so that the outer layer tends to radially contract and the inner layer tends to radially expand when the drive shaft is rotated in a predetermined direction; and drive shaft having proximal, intermediate and distal segments, wire turns of the proximal segment of the drive shaft having a generally constant diameter, wire turns of the intermediate segment of the drive shaft having a diameter that progressively increases distally through a proximal portion of such intermediate segment and having a diameter that progressively decreases distally through a distal portion of such intermediate segment, thereby defining an enlarged diameter segment of the drive shaft, at least part of the enlarged diameter intermediate segment including an external coating of an abrasive material to define an abrasive segment of the drive shaft.

112. The abrasive drive shaft atherectomy device comprising a flexible, elongated drive shaft having a central lumen for receipt of a guide wire therein around which the drive shaft may be rotated, the drive shaft being comprised of at least two helically wound wires forming inner and outer co-axial wire layer helically wound in opposite directions so that the outer layer tends to radially contract and the inner layer tends to radially expand when the drive shaft is rotated in a predetermined direction, the drive shaft having proximal, intermediate and distal segments; the outer wire layer extending along substantially the entire proximal segment of the drive shaft, terminating just proximal to the intermediate segment of the drive shaft and having a generally constant diameter, wire turns of the inner layer of the drive shaft extending along substantially the entire length of the drive shaft, such wire turns having a generally constant diameter along substantially the entire proximal segment of the drive shaft, having a diameter that progressively increases distally through a proximal portion of the intermediate segment, and having a diameter that progressively decreases distally through a distal portion of the intermediate segment, thereby defining an enlarged diameter segment of the drive shaft, at least part of the enlarged diameter intermediate segment including an external coating of an abrasive material to define an abrasive segment of the drive shaft.

113. The abrasive drive shaft atherectomy device comprising a flexible, elongated drive shaft having a central lumen for receipt of a guide wire therein around which the drive shaft may be rotated, the drive shaft being comprised of at least two helically wound wires forming inner and outer co-axial wire layers helically wound in opposite directions so that the outer layer tends to radially contract and the inner layer tends to radially expand when the drive shaft is rotated in a predetermined direction, the drive shaft having proximal intermediate and distal segments; the inner wire layer extending along substantially the entire length of the drive shaft and having a generally constant diameter; wire turns of the outer layer of the dive shaft extending along substantially all of the proximal and intermediate segments and at least partially along the distal segment of the drive shaft; such wire turns of the outer layer having a diameter that is substantially constant along substantially the entire proximal segment of the drive shaft, that progressively increases distally through a proximal portion of the intermediate segment, and that progressively decreases distally through a distal portion of the intermediate segment, thereby defining an enlarged diameter segment of the drive shaft, at least part of the enlarged diameter intermediate segment including an external coating of an abrasive material to define an abrasive segment of the drive shaft.

114. The abrasive drive shaft atherectomy device of claim 113 further comprising a toroidal collar positioned in the intermediate segment of the drive shaft and disposed between the inner and outer layers of the drive shaft.

* * * * *

UNITED STATES PATENT AND TRADEMARK OFFICE
CERTIFICATE OF CORRECTION

PATENT NO. : 5,314,438

DATED : May 24, 1994

INVENTOR(S) : Leonid Shturman

Page 1 of 2

It is certified that error appears in the above-identified patent and that said Letters Patent are hereby corrected as shown below:

Column 1, lines 37, 54, 57, 58, and 60, replace "buff" with --burr--.
Column 1, lines 40 and 41, replace "buffs" with --burrs--.
Column 1, line 46, replace "Striper's" with --Striper®--
Column 1, line 52, after "*Prosthetic*" insert --*Dentistry*--.
Column 2, line 2, replace "wail" with --wall--.
Column 2, lines 9, 11, 14, 17, 20, 26, 27, 33, 36, 40, 43, 50, 60, 64, 65, and 66, replace "buff" with --burr--.
Column 2, line 19, replace "buffs" with --burrs--.
Column 3, lines 2, 5, 10, 14, 16, 17, 18, 19, 23, and 25, replace "buff" with --burr--.
Column 3, line 53, replace "front" with --form--.
Column 4, lines 6, 41, 44, and 50, replace "buff" with --burr--.
Column 6, line 8, replace "180"" with --180°--.
Column 6, lines 40-41, replace "shaft-s" with --shafts--.
Column 7, line 44, replace "PHOTOLINKr" with --PHOTOLINK™--.
Column 9, line 46, replace "buffs" with --burrs--.
Column 10, line 29, after "TEFLON®" insert --)--.
Column 10, line 56, replace "comers" with --corners--.
Column 19, line 26, replace "to" with --so--.
Column 19, line 53, replace "proximally" with --proximal--.
Column 20, line 16, replace "within" with --with--.
Column 22, line 52, replace "48µm" with --45µm--.
Column 23, line 3, replace "haft" with --shaft--.
Column 23, line 22, replace "rive" with --drive--.
Column 24, line 52, replace "The" with --An--.
Column 24, line 61, replace "and" with --the--.
Column 25, line 6, replace "The" with --An--.
Column 25, line 11, replace "layer" with --layers--.
Column 25, line 20, replace "diameter," with --diameter;--.

UNITED STATES PATENT AND TRADEMARK OFFICE
CERTIFICATE OF CORRECTION

PATENT NO. : 5,314,438
DATED : May 24, 1994
INVENTOR(S) : Leonid Shturman

It is certified that error appears in the above-identified patent and that said Letters Patent are hereby corrected as shown below:

Column 26, line 11, after "-mal" insert --,-- .
Column 26, line 14, replace "dive" with --drive-- .

Signed and Sealed this

Twenty-third Day of September, 1997

Attest:

BRUCE LEHMAN

Attesting Officer

Commissioner of Patents and Trademarks